(12) United States Patent
Cyr

(10) Patent No.: US 7,481,993 B2
(45) Date of Patent: Jan. 27, 2009

(54) CHELATORS FOR RADIOACTIVELY LABELED CONJUGATES COMPRISING A STABILIZING SIDECHAIN

(75) Inventor: John E. Cyr, Berlin (DE)

(73) Assignee: Schering AG, Berlin (DE)

(*) Notice: Subject to any disclaimer, the term of this patent is extended or adjusted under 35 U.S.C. 154(b) by 0 days.

(21) Appl. No.: 11/371,241

(22) Filed: Mar. 9, 2006

(65) Prior Publication Data
US 2006/0263295 A1 Nov. 23, 2006

Related U.S. Application Data

(60) Provisional application No. 60/659,875, filed on Mar. 10, 2005.

(30) Foreign Application Priority Data
Mar. 10, 2005 (EP) ................................. 05005295

(51) Int. Cl.
*A61K 38/03* (2006.01)
*A61K 51/08* (2006.01)

(52) U.S. Cl. ...................... 424/1.69; 530/300; 530/345; 534/10; 534/14

(58) Field of Classification Search ........................ None
See application file for complete search history.

(56) References Cited

U.S. PATENT DOCUMENTS

| | | | | |
|---|---|---|---|---|
| 4,965,392 A * | 10/1990 | Fritzberg et al. | ............. | 558/254 |
| 5,112,953 A * | 5/1992 | Gustavson et al. | ........ | 530/391.5 |
| 5,804,157 A * | 9/1998 | Srinivasan et al. | .......... | 424/1.69 |
| 6,358,491 B1 | 3/2002 | Lister-James et al. | | |
| 2002/0001566 A1* | 1/2002 | Rajopadhye et al. | ........ | 424/1.69 |

FOREIGN PATENT DOCUMENTS

| | | |
|---|---|---|
| EP | 0719790 A | 7/1996 |
| WO | WO 01/13112 A | 2/2001 |
| WO | WO 02/064734 | 8/2002 |

OTHER PUBLICATIONS

Zhu, Z. et al., "A novel and spimplified route to the synthesis of N3S chelators for <00m>Tc labeling<1>," Nuclear Medicine and Biology, Aug. 2001, pp. 703-708, vol. 28 No. 6, Elsevier Science Publishers, NY, NY.

* cited by examiner

*Primary Examiner*—Jeffrey E Russel
(74) *Attorney, Agent, or Firm*—Millen, White, Zelano & Branigan, P.C.

(57) ABSTRACT

The invention relates to a conjugate PT comprising
(a) a peptide P and
(b) a targeting moiety T;
wherein the peptide P contains from 4 to 20 amino acid residues with optionally a single thiol moiety at the C- or N-terminus replacing one of these amino acid residues, and including a complexing amino acid sequence comprising
  (iv) a tridentate or tetradentate planar chelator containing a ligand backbone defined by a perimeter containing
    a single sulfur donor atom,
    two or three non-sulfur donor atoms, and
    intervening atoms between the donor atoms; and
  (v) a stabilizing sidechain comprising a further donor atom, the further donor atom being covalently linked to the ligand backbone of the planar chelator through two or three intervening atoms, provided that
    said further donor atom is neither the nitrogen nor the oxgen atom of a peptide bond and
    if said further donor atom is part of a heterocyclic ring, no more than one of the intervening atoms can be part of that ring; and
a radioactive metal complexed to the donor atoms of the planar chelator.

26 Claims, 3 Drawing Sheets

| Code | R1 | R2 |
|---|---|---|
| GGC1 | -H | -H |
| GMC | -H | -CH₂CH₂SCH₃ |
| GOC1 | -H | -CH₂CH₂CH₂NH₂ |
| GoC1 | -H | (D)-CH₂CH₂CH₂NH₂ |
| OGC | -CH₂CH₂CH₂NH₂ | -H |
| GQC | -H | -CH₂CH₂CONH₂ |
| GEC | -H | -CH₂CH₂COOH |

| Code | R1 | R2 |
|---|---|---|
| GGC2 | -H | -H |
| GOC2 | -H | -CH₂CH₂CH₂NH₂ |
| GoC2 | -H | (D)-CH₂CH₂CH₂NH₂ |
| MGC | -CH₂CH₂SCH₃ | -H |
| QGC | -CH₂CH₂CONH₂ | -H |
| EGC | -CH₂CH₂COOH | -H |
| OGC | (D)-CH₂CH₂CH₂NH₂ | -H |
| GRC | -(CH₂)₃NHC(NH₂)=NH | -H |
| GHC | -H |  |

Triamide Thiol (N¹-N²-Cys) Model Chelator Peptides cyclo[Phe-Tyr-D-Trp-Lys-Thr-Phe-(N-Me)Hcy]
+
ClCH$_2$CO-β-Dap-Orn-Cys(Trt)-Thr-Ser-OH ↓ 1:1 acetonitrile/0.15 M carbonate
pH 10.0

↓ 5% triisopropylsilane in 1:1 TFA/CH$_2$Cl$_2$ $^{99m}$Tc Somatostatin Peptides ⁹⁹ᵐTc Somatostatin Peptides;
Commercial Lung Cancer Diagnostic Agent Analogs Triamide Thiol ($N^1$-$N^2$-Cys) Model Chelator Peptides

| Code | R3 |
|---|---|
| Dap.GC1 | -H |
| Dap.OC | -CH$_2$CH$_2$CH$_2$NH$_2$ |
| Dap.oC | (D)-CH$_2$CH$_2$CH$_2$NH$_2$ |
| Dap.MC | -CH$_2$CH$_2$SCH$_3$ |

| Code | R4 |
|---|---|
| Dap.GC2 | -H |
| Dap-Y.GC | -COCH$_2$CH$_2$NH$_2$ |

Amine Diamide Thiol ((βDap-N$^2$-Cys) Model Chelator Peptides

| Code | R5 |
|---|---|
| Ma.GG | -H |
| Ma.oG | (D)-CH$_2$CH$_2$CH$_2$NH$_2$ |

Triamide Thiol (Ma-N$^1$-N$^2$) Model Chelator Peptides

CHELATORS FOR RADIOACTIVELY LABELED CONJUGATES COMPRISING A STABILIZING SIDECHAIN This application claims the benefit of the filing date of U.S. Provisional Application Ser. No. 60/659,875 filed Mar. 10, 2005 which is incorporated by reference herein.

The invention relates to peptides for use in diagnostic imaging, particularly to $^{99m}$Tc, $^{186}$Re, and $^{188}$Re labeled peptides. The radioactively labeled peptides comprise a complexing amino acid sequence which contains a planar chelator to which a radioactive metal is complexed. The peptides according to the invention are linked to a targeting moiety T which comprises a structural motif capable of selectively recognizing and binding to specific target molecules in a mammalian body.

In recent years, the emphasis in nuclear medicine has shifted toward targeted molecular imaging and therapy. In this approach, localized targets such as antigens, receptors, enzymes, or pathological phenotypes are targeted by radioactive isotopes to identify or treat a disease. Because the abundance of these molecular targets is often low, it is imperative to have very specific radiopharmaceuticals with high purity and high stability.

A variety of radionuclides are known to be useful for radioimaging and radiotherapy, including metals such as $^{67}$Ga, $^{68}$Ga, $^{99m}$Tc, $^{111}$In, $^{90}$Y, $^{177}$Lu, $^{64}$Cu, $^{188}$Re, and $^{186}$Re, and halides such as $^{18}$F, $^{123}$I, and $^{131}$I. The quality of a radiopharmaceutical preparation particularly in regard to yield and stability is often dictated by the quality of the radiolabeling method (i.e. the method for attaching the radiotracer to the targeting molecule). Direct methods are know in the prior art for adding radioiodine (e.g. H.-F. Beer, et al., (1993), *Nucl. Med. Biol.*, 20, 607) or radioactive Tc/Re (U.S. Pat. No. 5,061,641) to a biological molecule. However direct methods often show instability of the radioactive compound in vitro (i.e. poor shelf life) and in vivo (i.e. release of free radioiodide or pertechnetate/perrhenate in the patient). They have the additional disadvantage that the radiolabeling is not controlled in regard to site of attachment of the radioisotope, and in fact, the radioisotope can often add in more than one location on the molecule. The biological efficacy of the molecule can be affected if the radioisotope adds to a portion of the targeting molecule critical for binding to the target.

The use of chelating agents (chelators) for radiolabeling targeting molecules with radiometals can overcome many of the disavantages of direct radiolabeling methods. The chelators form stable metal complexes that attach the radiometal more reliably and stably onto the targeting molecule. In addition, the metal chelator can be added to the targeting molecule in a more defined manner with several options for point of attachment. Methods for labeling peptides, polypeptides, antibodies, and antibody fragments with radiometals using chelators have been disclosed in the prior art.

U.S. Pat. Nos. 5,164,176 and 5,250,666 disclose chelating compounds containing two sulfur donor atoms derived from two thiol groups, which together with two additional nitrogen donor atoms from amine or amide groups form an $N_2S_2$ tetratdenate chelator. These chelators are useful for radiolabeling targeting proteins such as antibodies. The radiolabeled antibodies, or catabolites thereof, demonstrate improved biodistribution properties, including reduced localization within the intestine.

U.S. Pat. No. 5,310,536 discloses $N_2S_2$ and $N_3S$ amide-thiolate ligands having improved metal chelate formation kinetics. The ligands include a tertiary amine strategically located to facilitate rapid formation of an amine-amide-thiolate intermediate complex. The rapidly formed intermediate complex then transfers the metal to a thermodynamically stable amide-thiolate core. Overall, the metal chelate formation kinetics are enhanced.

U.S. Pat. No. 6,093,383 discloses bisamine bisthiol chelators covalently linked to a specific binding peptides that have the advantage of forming an electrically neutral metal complexes with $^{99m}$Tc, thereby not interfering with the binding properties of the peptide.

Peptide-based radiometal chelators offer the advantages of easy synthesis and modification of the chelating ligand. Hence, the chelator is easily synthesized and can be conjugated to the targeting molecule using solid phase synthesis techniques. In addition, the chelator is easily modified by exchanging the amino acids comprising the chelator, or by adding additional amino acids adjacent to the chelator sequence. Peptide based chelators may also be incorporated into proteins during recombinant synthesis if the amino acids comprising the chelator are proteinergic. Several examples of peptide-based chelators have been disclosed in the prior art.

U.S. Pat. No. 5,849,261 discloses vasoactive intestinal peptide (VIP) receptor peptides and derivatives and analogues thereof covalently linked to peptide-based chelators for technetium and rhenium. Embodiments of such peptides labeled with γ-radiation emitting isotopes such as $^{99m}$Tc, as well as methods and kits for making, radiolabeling and using such peptides to image sites in a mammalian body are described.

U.S. Pat. No. 5,993,775 discloses scintigraphic imaging and radiotherapeutic agents that are radiocatively labeled peptides between 7 and 100 amino acid residues in size, comprised of a targeting amino acid sequence and a metal complexing amino acid sequence containing a single thiol. Further embodiments include technetium and rhenium complexes of these peptides.

U.S. Pat. No. 6,126,916 discloses metal binding ligands comprising two amino acids and containing sulfur donor atoms from a thiol and thiosemicarbazide group. These ligands may be coupled to peptides for use in methods of diagnosis and therapy. The peptide derivatives are readily labeled with radiometals, such as isotopes of rhenium or technetium, while retaining their ability to tightly bind specific peptide receptors.

U.S. Pat. Nos. 5,780,006 and 5,976,495 disclose a peptide-based radiometal chelator (and radiometal complexes) comprised of 3 amino acids including a single thiol that offers the advantage that it can incorporated into a peptide/protein-based radiophamaceutical using peptide synthesis techniques. Embodiments where the chelator is linked to targeting moieties are also disclosed, including peptides specific for sites of inflammation.

U.S. Pat. No. 6,358,491 discloses somatostatin receptor binding peptides and derivatives that are covalently linked to peptide-based radiometal chelators containing a single thiol.

However, investigations have revealed that the thermodynamic stability of the metal chelates of the prior art is not satisfactory. The complexes of the prior art tend to dissociate thereby deteriorating the signal intensity and the contrast of the radioimaging method. The shelf life of radipharmaceuticals employing the radiometal complexes of the prior art is often limited by this instability. In order to improve the stability and increase the shelf life of the radiometal complexes, larger amounts of ligand are often used in the radiolabeling preparation. However, this can lower the biological effectiveness of the product if it is receptor-targeting, because the excess ligand can compete with the radiolabeled compound for binding sites. Excipients (e.g. anti-radiolytics) are often employed to improve the stability of radiopharmaceuticals, which adds complexity to the product formulation.

Thus, there is a demand for radioactively labeled complexes which are thermodynamically more stable than the complexes of the prior art.

It is the object of the invention to provide chelators and compounds radiolabeled using these chelators which have advantages over the chelators and radiolabeled compounds of the prior art. In particular, it is an object of the invention to provide radiopharmaceuticals possessing radiometal complexes with improved thermodynamic stability.

It has been surprisingly found that the thermodynamic stability of a peptide-based chelator can be significantly increased when it is defined as a peptide P from 4 to 20 amino acid residues with optionally a single thiol moiety at the C— or N-terminus replacing one of these amino acid residues, and including a complexing amino acid sequence comprising
  (i) a tridentate or tetradentate planar chelator containing a ligand backbone defined by a perimeter containing
    a single sulfur donor atom,
    two or three non-sulfur donor atoms, and
    intervening atoms between the donor atoms; and
  (ii) a stabilizing sidechain comprising a further donor atom, the further donor atom being covalently linked to the ligand backbone of the planar chelator through two or three intervening atoms, provided that
    said further donor atom is neither the nitrogen atom nor the oxygen atom of a peptide bond and
    if said further donor atom is part of a heterocyclic ring, no more than one of the intervening atoms can be part of that ring; and
  (iii) a radioactive metal complexed to the donor atoms of the planar chelator.

This peptide P forms part of a conjugate PT which comprises the peptide P and a targeting. moiety T.

According to the above definition, the peptide P is defined as a sequence of 4-20 amino acids with optionally a single thiol moiety at the N— or C-terminus replacing one of the amino acids, wherein all of the residues and the single thiol moiety are joined together by amide bonds. In addition, the peptide P comprises amino acid residues forming the complexing amino acid sequence and other amino acid residues which are not directly involved in the complexation of the radioactive metal. These other amino acid residues can be present
a. to adjust the physical characteristics (e.g. lipophilicity, stability) of the radiopharmaceutical,
b. to adjust the biodistribution or clearance of the radiopharmaceutical,
c. to provide a spacer between the targeting moiety and chelator, or
d. to modify or enhance the targeting efficacy of the compound, but not provide the main contribution to binding at the target, which comes from the targeting moiety.

For the purpose of the specification an amino acid residue is a constituent of the complexing amino acid sequence if at least one of its atoms is directly involved in the complexation of the radioactive metal, i.e. if at least one of its atoms is a donor atom of the chelator or the stabilizing side chain.

Peptide P may be linear, branched, or cyclic.

Preferably, the complexing amino acid sequence comprises at least 1 but not more than 5 and more preferably at least 2 but not more than 4 amino acid or single thiol moiety residues. Most preferably, the complexing amino acid sequence consists of 3 amino acid or single thiol moiety residues.

The term "amino acid sequence" is defined as a polyamide obtainable by polycondensation of at least two amino acids, wherein "amino acid" means any molecule comprising at least one amino group and at least one carboxyl group, provided that, if the amino acid contains an amide group, said amide bond is not a peptide bond. Thus, a dipeptide having a free amino group at the N-terminus and a free carboxyl group at the C-terminus is not to be considered as a single "amino acid" in the above definition. The amide bonds between two adjacent amino acid residues which are obtained from such a polycondensation are defined as "peptide bonds". Optionally, the nitrogen atoms of the polyamide backbone may be independently alkylated, e.g. with —$C_1$-$C_6$-alkyl, preferably —$CH_3$.

For the purpose of the specification an amino acid residue is derived from the corresponding amino acid by forming a peptide bond with another amino acid.

For the purpose of the specification an amino acid sequence may comprise naturally occurring and/or artificial amino acid residues, proteinogenic and/or non-proteinogenic amino acid residues. The non-proteinogenic amino acid residues may be further classified as (a) homo analogues of proteinogenic amino acids, (b) β-homo analogues of proteinogenic amino acid residues and (c) further non-proteinogenic amino acid residues.

The amino acid sequences according to the invention may be linear, branched or cyclic.

Accordingly, the amino acid residues are derived from the corresponding amino acids, e.g. from
  proteinogenic amino acids, namely Ala, Arg, Asn, Asp, Cys, Gln, Glu, Gly, His, Ile, Leu, Lys, Met, Phe, Pro, Ser, Thr, Trp, Tyr and Val; or
  non-proteinogenic amino acids, such as
    homo analogues of proteinogenic amino acids wherein the sidechain has been extended by a methylene group, e.g. Homoalanine (Hal), Homoarginine (Har), Homocysteine (Hcy), Homoglutamine (Hgl), Homohistidine (Hhi), Homoisoleucine (Hil), Homoleucine (Hle), Homolysine (Hly), Homomethionine (Hme), Homophenylalanine (Hph), Homoproline (Hpr), Homoserine (Hse), Homothreonine (Hth), Homotryptophane (Htr), Homotyrosine (Hty) and Homovaline (Hva);
    β-homo analogues of proteinogenic amino acids wherein a methylene group has been inserted between the α-carbon and the carboxyl group yielding β-amino acids, e.g. β-Homoalanine (βHal), β-Homoarginine (βHar), β-Homoasparagine (βHas), β-Homocysteine (βHcy), β-Homoglutamine (βHgl), β-Homohistidine (βHhi), β-Homoisoleucine (βHil), β-Homoleucine (βHle), β-Homolysine (βHly), β-Homomethionine (βHme), β-Homophenylalanine (βHph), β-Homoproline (βHpr), β-Homoserine (βHse), β-Homothreonine (βHth), β-Homotryptophane (βHtr), β-Homotyrosine (βHty) and β-Homovaline (βHva);
    further non-proteinogenic amino acids, e.g. α-Aminoadipic acid (Aad), β-Aminoadipic acid (βAad), α-Aminobutyric acid (Abu), α-Aminoisobutyric acid (Aib), β-Alanine (βAla), 4-Aminobutyric acid (4-Abu), 5-Aminovaleric acid (5-Ava), 6-Aminohexanoic acid (6-Ahx), 8-Aminooctanoic acid (8-Aoc), 9-Aminononanoic acid (9-Anc), 10-Aminodecanoic acid (10-Adc), 12-Aminododecanoic acid (12-Ado), α-Aminosuberic acid (Asu), Azetidine-2-carboxylic acid (Aze), β-Cyclohexylalanine (Cha), Citrulline (Cit), Dehydroalanine (Dha), γ-Carboxyglutamic acid (Gla), α-Cyclohexylglycine (Chg), Propargylglycine (Pra), Pyroglutamic acid (Glp), α-tert-Butylglycine (Tle), 4-Benzoylphenylalanine (Bpa), δ-Hydroxylysine (Hyl), 4-Hydroxyproline (Hyp), allo-Isoleucine (alle), Lanthionine (Lan), (1-naphthyl) alanine (1-Nal), (2-naphthyl)alanine (2-Nal), Norleucine (Nle), Norvaline (Nva), Ornithine (Orn), Phenylglycin (Phg), Pipecolic acid (Pip), Sarcosine (Sar), Selenocysteine (Sec), Statine (Sta), β-Thienylalanine (Thi), 1,2,3,4-Tetrahydroisochinoline-3-carboxylic acid (Tic), allo-Threonine (aThr), Thiazolidine-4-carboxylic acid (Thz), γ-Aminobutyric acid (GABA), iso-Cysteine (iso-Cys), Diaminopropionic acid (Dap), 2,4-Diaminobutyric acid (Dab), 3,4-Diaminobutyric acid (γ,βDab), Biphenylalanine (Bip), Phenylalanine substituted in para-position with —$C_1$-$C_6$-alkyl, -halide, —$NH_2$ or —$CO_2H$ (Phe(4-R) wherein R=—$C_1$-$C_6$-alkyl, -halide, —$NH_2$, or —$CO_2H$); peptide nucleic acids (PNA, cf. P. E. Nielsen, Acc.Chem.Res. 32, 624-30)

or their N-alkylated analogues, such as their N-methylated analogues.

Cyclic amino acids may be proteinogenic or non-proteinogenic, such as Pro, Aze, Glp, Hyp, Pip, Tic and Thz.

For further examples and details it can be referred to e.g. J. H. Jones, J. Peptide Sci. 2003, 9, 1-8 which is incorporated herein by reference.

The terms "non-proteinogenic amino acid" and "non-proteinogenic amino acid residue" also encompasses derivatives of proteinogenic amino acids. For example, the sidechain of a proteinogenic amino acid residue may be derivatized thereby rendering the proteinogenic amino acid residue "non-proteinogenic". The same applies to derivatives of the C-terminus and/or the N-terminus of a proteinogenic amino acid residue terminating the amino acid sequence.

For the purpose of the specification a proteinogenic amino acid residue is derived from a proteinogenic amino acid selected from the group consisting of Ala, Arg, Asn, Asp, Cys, Gln, Glu, Gly, His, Ile, Leu, Lys, Met, Phe, Pro, Ser, Thr, Trp, Tyr and Val either in L- or D-configuration; the second chiral center in Thr and Ile may have either R- or S-configuration. Therefore, for example, any posttranslational modification of an amino acid sequence, such as N-alkylation, which might naturally occur renders the corresponding modified amino acid residue "non-proteinogenic", although in nature said amino acid residue is incorporated in a protein.

According to the above definition, the single sulfur donor atom can come from a single thiol-containing amino acid or from a single thiol moiety, where the single thiol moiety is defined as a non-amino acid structure bearing a single thiol which is capable of forming amide bonds. Preferred examples of single thiol amino acids are Cys and iso-Cys. Preferred examples of the single thiol moiety are mecaptoacetyl (Ma), 2-mercapto-propionyl (Mp), 2-mercapto-2-methylpropionyl (Mmp), 2-mercapto-propylamino (Mpa), 2-aminoethanethiol (Aet), 2-Amino-propanethiol (Apt), and 2-mercapto-2-methylpropylamino (Mma).

The peptide P may comprise e.g. α-amino acid residues, i.e. amino acid residues of general formula —$NR^a$—$CR^bR^c$—CO—, and/or β-homo amino acid residues, i.e. amino acid residues of the general formula —$NR^aCR^bR^c$—$CH_2$—CO—, and/or ω-amino alkyl carboxylic acids of the general formula —$NR^a$—$(CR^bR^c)_n$—CO— where n=2-12, and/or diamino acids of the general formulas —$NR^a$—$CR^bR^c$—$CR^d(NR^e)$—$(CR^fR^g)_n$—CO— or —$NR^a$—$(CR^bR^c)_n$—$CR^d(NR^e)$—CO— where n=1-10, and/or a single thiol moiety, wherein $R^a$, $R^b$, $R^c$, $R^d$, $R^e$, $R^f$, and $R^g$ may be any moiety capable of being covalently linked to a carbon or nitrogen atom.

When an amino acid residue comprises more than a single amino group, any of the amino groups may be involved in the peptide bond to an adjacent amino acid residue. For example, the amino acid residue of lysine may be covalently linked either through its α-amino group or its ε-amino group. The same applies to amino acid residues comprising more than a single carboxyl group, i.e. any of the carboxy groups may be involved in the peptide bond to an adjacent amino acid residue. For example, the amino acid residue of glutamic acid may be covalently linked either through its α-carboxy group or its δ-carboxy group. Branching of the amino acid sequence may be effected if, for example, both carboxy groups of glutamic acid are covalently linked to the N-terminus of 2 amino acids or amino acid sequences.

Preferably, the peptide P does not comprise more than 10 amino acid residues which are other than α-amino acid residues, more preferably not more than 6, most preferably not more than 4, in particular not more than 2 amino acid residues which are other than α-amino acid residues. In a preferred embodiment, all amino acid residues contained in the peptide P are α-amino acid residues.

Chiral amino acid residues may be present in racemic form, preferably, however, in the pure enantiomeric form. For the purpose of the specification "pure anantiomeric form" means preferably >95% ee, more preferably >98% ee, in particular >99% ee.

The peptide P comprises at least 4 but not more than 20 amino acid residues including single thiol moieties. In a preferred embodiment peptide P comprises at least 6, but not more than 15, more preferably not more than 10, and most preferably not more than 8 amino acid residues including single thiol moieties.

The planar chelator of the complexing amino acid sequence of the peptide P can be tridentate or tetradentate. The term "planar" refers to the plane formed by donor atoms contained in the ligand backbone, and the number of donor atoms utilized by the chelator being 3 or 4 classifies the chelator as tridentate or tetradentate, respectively. In the case that during complexation to the metal all donor atoms of the chelator lie substantially in the same plane, the chelator is a planar chelator. Further atoms of the planar chelator do not have to but may also lie substantially in the same plane as the donor atoms of the planar chelator. As tridentate chelators only comprise three donor atoms in the ligand backbone, tridendate chelators are always planar chelators in the definition according to the invention (three coordinates in the Cartesian space always lie in a plane). Tetradendate chelators are planar chelators in the definition according to the invention, when during complexation to the metal all four donor atoms of the ligand backbone lie substantially in the same plane.

Preferably, in tetradentate chelators the sulfur donor atom of the ligand backbone is not more than 200 pm, more preferably not more than 125 pm, most preferably not more than 75 pm out of the plane which is formed by the three non-sulfur donor atoms of the planar chelator.

It is well-known that technetium(V) oxo and rhenium (V) oxo metal cores form predominantly 5-coordinate pseudo-square pyramidal complexes with planar chelators comprising 4 donor atoms. These complexes have configurations in which the 4 donor atoms of the ligand lie approximately in a plane at the base of the pyramid, and the separate fifth oxo ligand occupies the apex of the pyramid. The planar ligand set describing the base of the pyramid can come from one tetradentate ligand, or from a combination of a tridentate ligand along with a monodentate ligand (a "3+1" ligand system). Other radiometals such as Cu, Pt, or Pd are also known to have planar ligand coordination environments involving 4 donor atoms.

The non-sulfur donor atoms of the planar chelator may be any atom capable of coordinating to a metal, preferably through a dative bond, except sulfur atoms. Lewis bases are generally suitable for that purpose. In a preferred embodiment of the peptide P the non-sulfur donor atoms are donor atoms independently selected from the group consisting of nitrogen, phosphorus, arsenic and oxygen; more preferably, all non-sulfur donor atoms are nitrogen donor atoms. Depending on the radioactive metal complexed to the complexing amino acid sequence, the donor atoms may optionally and independently be deprotonated.

The intervening atoms between the donor atoms, i.e. the intervening atoms along the perimeter of the ligand backbone between the single sulfur donor atom and the two or three non-sulfur donor atoms, may be any atoms capable of forming covalent bonds with the donor atoms. Preferably, along the perimeter of the ligand backbone all intervening atoms are carbon atoms. More preferably, two neighbored donor atoms are spaced by two or three carbon atoms.

The ligand backbone of the planar chelator may form a closed cycle. Preferably, however, the ligand backbone of the planar chelator is an open chain, which preferably may be terminated on one end by the single sulfur atom in form of its thiol. More preferably, the perimeter of the ligand backbone of the planar chelator is derived from the following (further substituted) molecular chain:

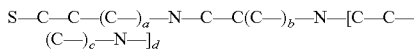

wherein the indices a, b, c and d are independently 0 or 1. Most preferably, the indices a, b and c are 0 and the index d is 1.

In the chelator metal complexes of this invention, the further donor atom of the stabilizing sidechain does not have to lie substantially in the same plane as the donor atoms of the planar chelator. Preferably, the further donor atom of the stabilizing sidechain is significantly out of the plane which is formed by the three or four donor atoms of the planar chelator. Without wishing to be bound to any theory, it is assumed that the further donor atom of the stabilizing sidechain occupies a vacant coordination site of the metal perpendicular to the ligand plane and in the case of the Tc(V) or Re(V) oxo species, the sixth coordination site opposite the oxo group. The additional coordination of the metal is expected to impart greater thermodynamic stability to the metal complex. The ability of a stabilizing sidechain to coordinate at the additional site perpendicular to the ligand plane is most certainly determined for steric reasons by the length of the sidechain. It is apparent that the most preferred sidechain length to position the donor atom properly for metal coordination is 3-4 atoms from the ligand backbone to the donor atom. Given the approximate symmetry of the atoms in the planar ligand backbone about the metal, it is further assumed that any position about the ligand backbone should be suitable for attaching the stabilizing sidechain.

In a preferred embodiment the further donor atom of the stabilizing sidechain is not a tertiary amine nitrogen donor atom.

Preferably, the planar chelator comprises a single thiol amino acid or a single thiol moiety containing the single sulfur donor atom of the ligand backbone, the single thiol amino acid or single thiol moiety having a structure represented by general formula (I):

wherein
A is $-CO_2H$, $-CONH_2$, $-CO_2$-(pep), $-CONH$-(pep), or $R^4$;
B is $-SH$, $-NHR^3$, $-N(R^3)$-(pep), or $R^4$;
X is $-SH$, $-NHR^3$, $-N(R^3)$-(pep), or $R^4$;
Z is $-H$ or $-CH_3$;
n is 0, 1, or 2;
$R^1$, $R^2$, $R^3$, and $R^4$ are independently $-H$ or $-C_1$-$C_6$-alkyl;
(pep) represents the remainder of the peptide P and its complexing amino acid sequence, respectively;
provided that either
(a) B is $-NHR^3$ or $-N(R^3)$-(pep); X is $-SH$; and n is 1 or 2; or
(b) B is $-SH$; X is $-NHR^3$ or $-N(R^3)$-(pep); and n is 1 or 2; or
(c) A is $-CO_2$-(pep) or $-CONH$-(pep); B is $R^4$; X is $-SH$ and n is 0 or 1; or
(d) A is $R^4$; B is $-SH$; and X is $-N(R^3)$-(pep); or
(e) A is $R^4$; B is $-N(R^3)$-(pep); and X is $-SH$; or
(f) A is $-CO_2$-(pep) or $-CONH$-(pep); B is $-SH$; and X is $R^4$; or
(g) A is $-CO_2$-(pep) or $-CONH$-(pep); B is $-SH$; X is $-CH_3$; Z is $-CH_3$; and n is 0;
and provided that at least one moiety (pep) is present.
Preferably, either
(a) A is $-CONH$-(pep); B is $-N(R^3)$-(pep); X is $-SH$; Z is $-H$; n is 1; and $R^1$, $R^2$ and $R^3$ are $-H$; or
(b) A is $-CONH$-(pep); B is $-SH$; X is $-N(R^3)$-(pep); Z is $-H$; n is 1; and $R^1$, $R^2$ and $R^3$ are $-H$; or
(c) A is $-CONH$-(pep); B is $-H$ or $-CH_3$; X is $-SH$; Z is $-H$; and n is 0; or
(d) A is $-CH_3$; B is $-SH$; X is $-N(R^3)$-(pep); Z is $-H$; n is 1; and $R^1$, $R^2$ and $R^3$ are $-H$; or
(e) A is $-CH_3$; B is $-N(R^3)$-(pep); X is $-SH$; Z is $-H$; n is 1; and $R^1$, $R^2$ and $R^3$ are $-H$; or
(f) A is $-CONH$-(pep); B is $-SH$; X is $-H$ or $-CH_3$; Z is $-H$; and n is 0; or
(g) A is $-CONH$-(pep); B is $-SH$; X is $-CH_3$; Z is $-CH_3$; and n is 0.

In another preferred embodiment of the peptide according to the invention the single thiol moiety has a structure represented by general formula (I) wherein
(a) where B is $-NHR^3$ or $-N(R^3)$-(pep): X is $-SH$; and n is 1 or 2;
(b) where X is $-NHR^3$ or $-N(R^3)$-(pep): B is $-SH$; and n is 1 or 2;
(c) where B is $R^4$: A is $-CO_2H$, $-CONH_2$, $-CONH$-(pep), or $-CO_2$-(pep); X is $-SH$; and n is 0 or 1;
(d) where A is $R^4$ and where B is $-SH$: X is $-NHR^3$ or $-N(R^3)$-(pep); and
(e) where A is $R^4$ and where X is $-SH$: B is $-NHR^3$ or $-N(R^3)$-(pep);
(f) where X is $R^4$: A is $-CO_2H$, $-CONH_2$, $-CONH$-(pep), or $-CO_2$-(pep); and B is $-SH$; and
(g) where Z is $-CH_3$: X is $-CH_3$; A is $-CO_2H$, $-CONH_2$, $-CONH$-(pep), or $-CO_2$-(pep); B is $-SH$; and n is 0;

provided that at least one moiety (pep) is present.

Preferred examples of the single thiol amino acids having the structure represented by the general formula (I) are:

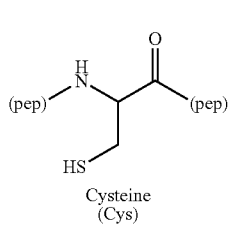
Cysteine
(Cys)

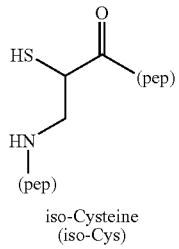
iso-Cysteine
(iso-Cys)

Preferred examples of the single thiol moiety having a structure represented by general formula (I) are:

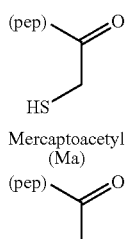
Mercaptoacetyl
(Ma)

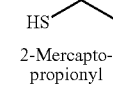
2-Mercapto-
propionyl
(Mp)

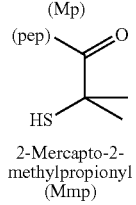
2-Mercapto-2-
methylpropionyl
(Mmp)

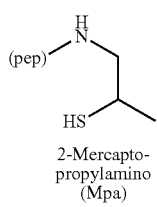
2-Mercapto-
propylamino
(Mpa)

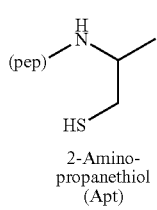
2-Amino-
propanethiol
(Apt)

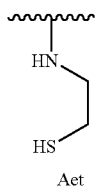
Aet

-continued

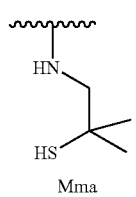
Mma

The complexing amino acid sequence may also comprise further sulfur atoms, e.g. thioethers. Preferably, such sulfur atoms are contained in the stabilizing sidechain as further donor atoms. For example, the thioether group of methionin may serve as further donor atom in the stabilizing sidechain linked to the ligand backbone of the planar chelator.

Preferably the complexing amino acid sequence should contain an amino acid capable of contributing an amine nitrogen to the planar ligand donor set. Diamine amino acids of this type are represented by the general formulas:

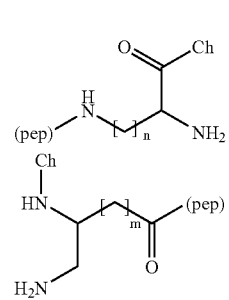

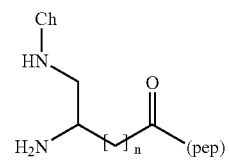

wherein (pep) represents the remainder of the peptide P, Ch represents the remainder of the complexing amino acid sequence and optionally in addition further remaining peptide, the index n=1-10, and the index m=0-10. In the most preferred embodiments of the above diamne amino acid general formulas, n=1 and m=0.

For the purposes of the specification, diamine amino acids are labeled with a greek letter in parentheses to signify the amine which is bonded to the remainder of the peptide or the remainder of the complexing amino acid sequence (e.g. (β)Dap; see the structure below). If the attachment to the remainder of the peptide or to the complexing amino acid sequence in a diamine amino acid is at a normal alpha amine, then normally no greek letter is required [(α)Dap=Dap]. In addition, greek letters not in parentheses signify the position of the amine group (or groups) in amino acids where an amine group does not occupy the normal alpha position (e.g. 3-amino propionic acid=β-Ala). As further examples, the preferred diamine amino acids from above are:

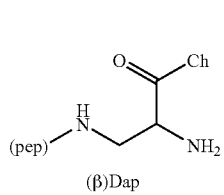
(β)Dap

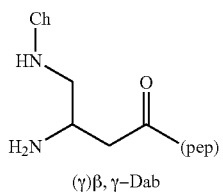
(γ)β, γ–Dab

-continued

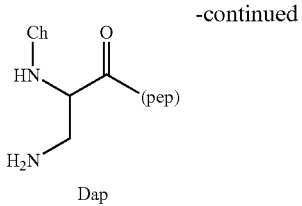

Dap

In a preferred embodiment the peptide P comprises a complexing amino acid sequence containing a structure represented by general formula (II)

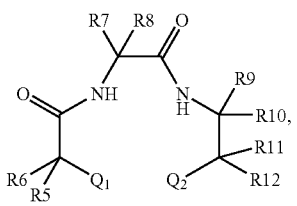

(II)

wherein
Q$_1$ is —SH, and Q$_2$ is either —N-(pep), or —N-(sidechain), or —NR$_2$ wherein R is independently —H or —C$_1$-C$_6$-alkyl; or
Q$_2$ is —SH, and Q$_1$ is either —N-(pep), or —N-(sidechain), or —NR$_2$ wherein R is independently —H or —C$_1$-C$_6$-alkyl;
R$^5$ and R$^6$ are independently E, -(pep) or -(sidechain);
R$^7$, R$^8$, R$^9$ and R$^{10}$ are independently E, -(pep) or -(sidechain); and
R$^{11}$ and R$^{12}$ are independently E or -(pep), or R$^{11}$ and R$^{12}$ together with the carbon atom to which they are attached form a carbonyl group;
wherein
E is independently selected from the group consisting of —H, —C$_1$-C$_4$-alkyl, —CH$_2$OH, —CH$_2$NH$_2$, —CH(OH)CH$_3$, —CH$_2$C$_6$H$_5$, —CH$_2$CH$_2$C$_6$H$_5$, —CH$_2$-(p-C$_6$H$_4$—OH), —CH$_2$-(p-C$_6$H$_4$—NH$_2$), —CH$_2$-(p-C$_6$H$_4$—F), —CH$_2$-(p-C$_6$H$_4$—Cl), —CH$_2$-(p-C$_6$H$_4$—I), —CH$_2$-(p-C$_6$H$_4$—Br), —CH$_2$CH$_2$—CH$_2$CH$_2$NH$_2$, —CH$_2$-(3-indolyl), —CH$_2$CH$_2$CH$_2$COOH, —CH$_2$CH$_2$CH$_2$—CH$_2$CH$_2$CH$_2$—COOH, —CH$_2$C$_6$H$_{11}$, —CH$_2$SCH$_2$CH(COOH)NH$_2$, —C$_6$H$_5$, —CH$_2$-(1-napthyl), —CH$_2$-(2-napthyl), —C$_6$H$_{11}$, —CH$_2$C≡CH, —C(CH$_3$)$_3$, —CH$_2$-(p-C$_6$H$_4$—COC$_6$H$_5$), —CH$_2$-(p-C$_6$H$_4$—C$_6$H$_5$);
(pep) represents the remainder of the peptide P and its complexing amino acid sequence; and
(sidechain) represents the stabilizing sidechain comprising a further donor atom;
provided that the structure represented by general formula (II) comprises at least one moiety (pep) and at least one moiety (sidechain).
Preferably, the structure represented by general formula (II) comprises only one moiety (sidechain).
In a preferred embodiment the complexing amino acid sequence comprises a sequence selected from the group consisting of
(pep)-N$^1$—N$^2$—C-(pep); (pep)-N$^1$—N$^2$—C; N$^1$—N$^2$—C-(pep); (pep)-N$^1$—N$^2$-Aet, (pep)-N$^1$—N$^2$-Aet(sidechain1), (pep)-N$^1$—N$^2$-Aet(sidechain2), (pep)-N$^1$—N$^2$-Apt, (pep)-N$^1$—N$^2$-Apt(sidechain), (pep)-N$^1$—N$^2$-Mpa, (pep)-N$^1$—N$^2$-Mpa(sidechain1), (pep)-N$^1$—N$^2$-Mpa(sidechain2); (pep)-N$^1$—N$^2$-Mma, (pep)-N$^1$—N$^2$-Mma(sidechain), (pep)-C—N$^2$—N$^3$; C—N$^2$—N$^3$-(pep), Ma-N$^2$—N$^3$-(pep), Ma(sidechain)-N$^2$—N$^3$-(pep), Mp-N$^2$—N$^3$-(pep), Mp(sidechain)-N$^2$—N$^3$-(pep), Mmp-N$^2$—N$^3$-(pep);
wherein
(pep) is the remainder of the peptide P;
C is selected from the group consisting of D-Cys, L-Cys, (R) iso-Cys, (S) iso-Cys and sidechain-substituted Cys or iso-Cys represented by the general formulas:

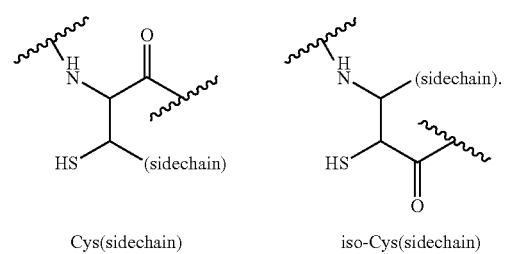

Cys(sidechain)  iso-Cys(sidechain)

Mp means 2-mercaptopropionyl;
Ma means 2-mercaptoacetyl;
Mpa means 2-mercaptopropylamino,
Apt means 2-amino-propanethiol;
Mmp means 2-mercapto-2-methyl-propionyl;
Aet means 2-amino-ethanethiol;
Mma means 2-mercapto-2-methylpropylamino;
Aet(sidechain1), Aet(sidechain2), Apt(sidechain), Mpa(sidechain1), Mpa(sidechain2), and Mma(sidechain) mean sidechain-substituted Aet, Apt, Mpa, and Mma, respectively, as represented by the general formulas:

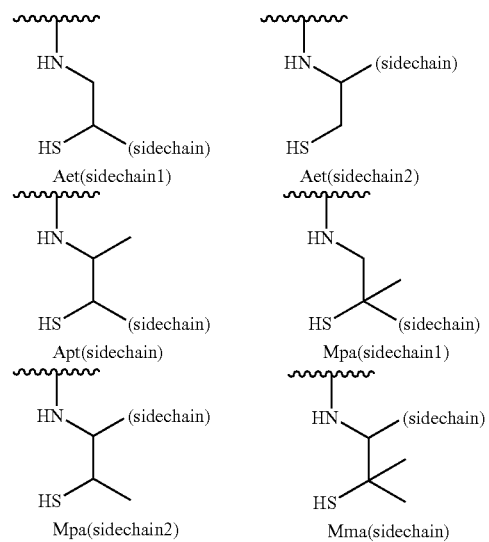

Ma(sidechain) and Mp(sidechain) mean sidechain-substituted Ma and Mp, respectively, as represented by the general formulas:

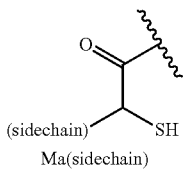
Ma(sidechain)

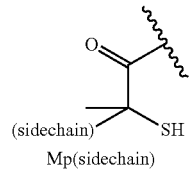
Mp(sidechain)

—N$^1$—, —N$^2$— and —N$^3$— are independently (i) an α- or β-(homo) amino acid residue with 0, 1 or 2 hydrocarbon sidechains that are saturated or unsaturated, and linear, branched, homocyclic, or heterocyclic, and optionally comprising one or more functional groups selected from hydroxyl, carbonyl, ether, thioether, carboxyl, amide, amine, nitro, nitroso, azido, aldehyde, ketone, aryl (preferably phenyl, napthyl), heteroaryl (preferably imidazolyl, pyrrolyl, furyl, thienyl, indolyl or pyridyl), halide, ester, cyano, glycosyl; or (ii) a heterocyclic amine-containing amino acid residue that is a saturated or unsaturated hydrocarbon, and optionally comprising one or more functional groups selected from hydroxyl, carbonyl, ether, thioether, carboxyl, amide, amine, nitro, nitroso, azido, aldehyde, ketone, aryl (preferably phenyl, napthyl), heteroaryl (preferably imidazolyl, pyrrolyl, furyl, thienyl, indolyl or pyridyl), halide, ester, cyano, glycosyl; or (iii) an amino acid residue represented by the general formulas (IIIa), (IIIb) and (IIIc)

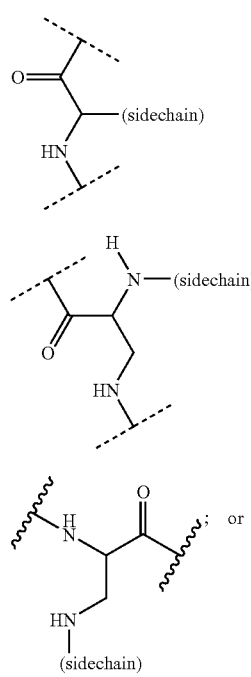

—N$^1$— is a ω-amine-linked D- or L-diamino acid of the general structure HOOC—CH(NH$_2$)—(CH$_2$)p-NH$_2$, or —N$^3$— is D-Dap, L-Dap, D-(β)Dap, L-(β)Dap or a ω-amine-linked amino acid of the general structure HOOC—(CH$_2$)$_p$—CH(NH$_2$)CH$_2$—NH$_2$, wherein index p is an integer of 1 to 10, and wherein the remainder of the peptide toward the N-terminus is linked at either amine group, wherein (β)Dap means β-diaminopropionic acid;

wherein
when —N$^1$—, —N$^2$— or —N$^3$— are α- or β-(homo) amino acids and when there is an appropriate chiral carbon atom, then they can be optionally D- or L-; and when —N$^1$— or —N$^2$— are α- or β-(homo) amino acids, then they can also optionally be in the N—C$_1$-C$_6$-alkyl form.

Preferably, either
—N$^1$— is Gly and —N$^2$— is an amino acid residue selected from the group consisting of Met, Orn, (D)Orn, Gln, Glu, Arg, and His; or —N$^1$— is an amino acid residue selected from the group consisting of Met, Orn, (D)Orn, Gln, Glu, Arg, His and (β)Dap(COCH$_2$CH$_2$NH$_2$) and —N$^2$— is Gly; or —N$^2$— is Gly and —N$^3$— is an amino acid residue selected from the group consisting of Met, Orn, (D)Orn, Gln, Glu, Arg, and His; or —N$^2$— is an amino acid residue selected from the group consisting of Met, Orn, (D)Orn, Gln, Glu, Arg, and His and —N$^3$— is Gly;

wherein (β)Dap(COCH$_2$CH$_2$NH$_2$) represents an amino acid residue represented by general formula (IIIb), wherein -(sidechain) is —COCH$_2$CH$_2$NH$_2$.

Preferred examples of the sequences which are comprised by the complexing amino acid sequence of the peptide according to the invention are summarized here below:

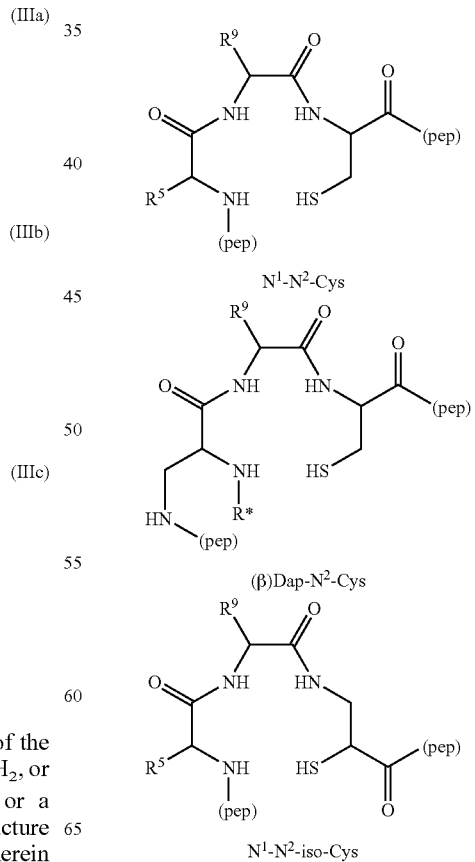

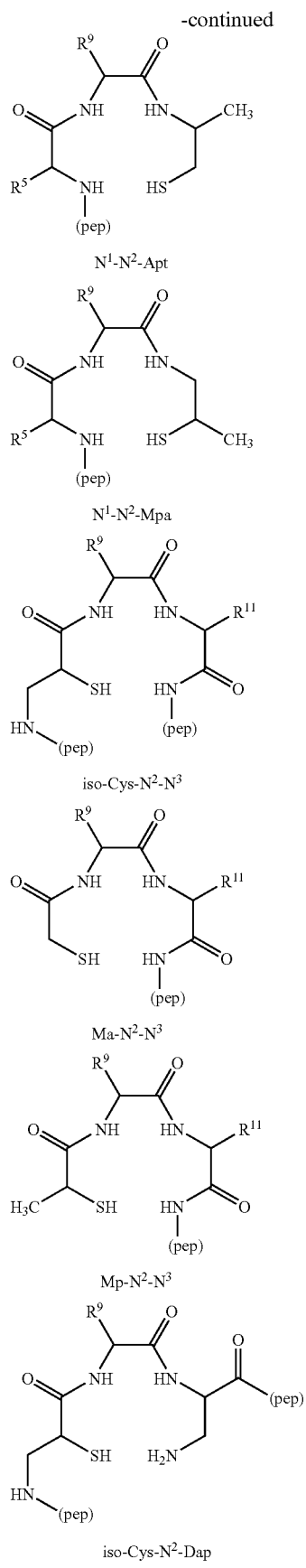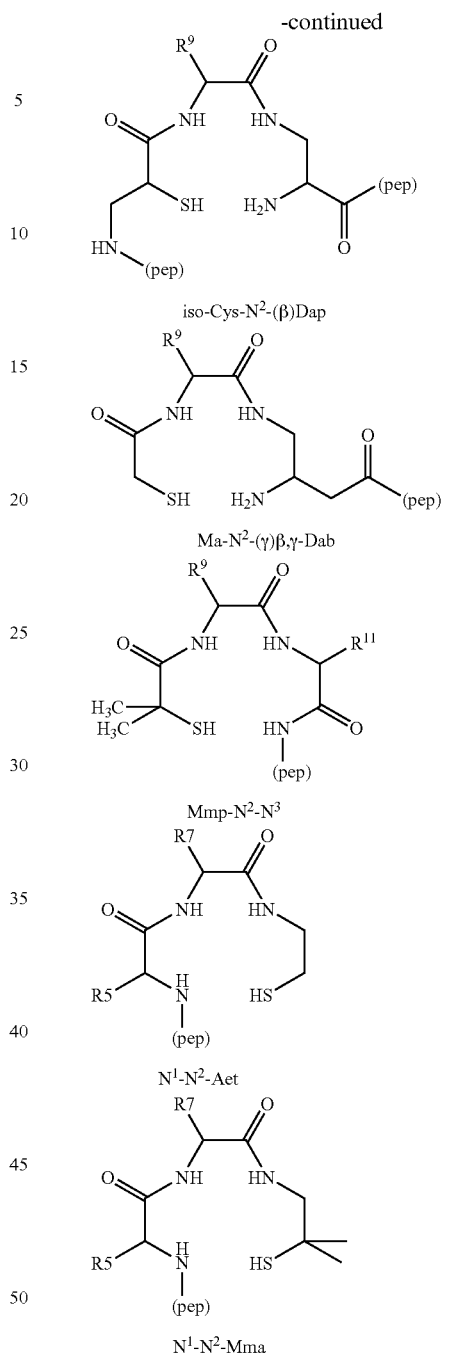

(β)Dap = β-diaminopropionyl
(γ)β,γDab = 3,4-diaminobutyryl
Mp = 2-mercaptopropionyl
Ma = mercaptoacetyl
Mpa = 2-mercaptopropylamino
Apt = 2-amino-propanethiol
Mmp = 2-Mercapto-2-methylpropionyl
Acet = 2-amino-ethanethiol
Mma = 2-mercapto-2-methylpropylamino In the preferred sequences depicted above R*, $R^5$, $R^9$ and $R^{11}$ are independently E or -(sidechain), wherein E and -(sidechain) are defined as in general formula (II) above; provided that at least one moiety (sidechain) is present. Preferably, E is —H.

A particularly attractive feature of peptide-based chelators is that amino acids within the chelator can be easily varied in order to modify the properties of the ligand-metal complex or moreover, a metal complex-targeting moiety conjugate. Exchanging amino acids in the chelator during solid phase syntheis effectively changes the substituents appended to the complex at the alpha positions of the amino acid carbons, while maintaining the backbone structure and donor atoms needed to complex the metal. Variation of the chelator amino acids therefore can be a useful tool during structure-activity optimization programs to improve the biological efficacy, clearance, pharmacokinetics, biodistribution, or chemical properties of metal-based peptide radiopharmaceuticals (for example: Cyr, J. E., et al., Development of an SSTR-targeting radiotherapy agent: Re-188 P2045, in *Technetium, Rhenium and Other Metals in Chemistry and Nuclear Medicine*, ed. M. Nicolini and U. Mazzi (Padova, Servizi Grafici Editoriali, 2002) p. 345). Peptide chelators bearing stabilizing side chains attached at the amino acid alpha carbons have the disavantage that the key amino acid positions are made unavailable for further variation. Hence, in a further embodiment the stabilizing sidechain is preferably attached to the ligand backbone at positions other than the standard amino acid alpha carbon positions, leaving the alpha carbon amino acid postions available for structural modification through amino acid substitution.

The peptide P contains a stabilizing sidechain comprising a further donor atom, the further donor atom being covalently linked to the ligand backbone of the planar chelator through two or three intervening atoms. The further donor atom of the stabilizing sidechain may be any atom capable of coordinating to a metal, preferably through a dative bond. Lewis bases are generally suitable for that purpose. In a preferred embodiment of the peptide according to the invention the further donor atom of the stabilizing sidechain is an atom selected from the group consisting of nitrogen, phosphor, oxygen and sulfur. The stabilizing sidechain may comprise more than a single further donor atom. If, for example, two further donor atoms are present in the stabilizing sidechain it is also possible that both further donor atoms fulfill the requirement of being linked to the ligand backbone of the planar chelator through 2 or 3 intervening atoms. For example, in the stabilizing sidechain —CH$_2$CH$_2$C(=NH)NH$_2$ both nitrogen atoms are linked to the ligand backbone of the planar chelator through 3 intervening carbon atoms.

However, it is not required that all further donor atoms satisfy this condition. For example, in the stabilizing sidechain —COCH$_2$CH$_2$NH$_2$ only the nitrogen donor atom fulfills the requirement of being linked to the ligand backbone of the planar chelator through 2 or 3 intervening atoms, as the oxygen atom is only linked through 1 intervening atom.

Preferably, the further donor atom of the stabilizing sidechain is an atom selected from the group consisting of N, P, O and S. Most preferably, the further donor atom is N.

According to the definition of the peptide P, the further donor atom contained in the stabilizing sidechain may be neither the nitrogen atom nor the oxygen atom of a peptide bond (—NHCO—) of the peptide P.

For the purpose of the specification, a peptide bond is defined as an amide bond linking two adjacent amino acid residues. Therefore, on the one hand the oxygen atom or the nitrogen atom of the side chain —CH$_2$CH$_2$CONH$_2$ is to be regarded as a further donor atom, as the amide bond is not a peptide bond, i.e. does not link two adjacent amino acid residues. Similarly, for example, the nitrogen atom of the N-terminus of the peptidic chelator "NNNC—" depicted here below is to be regarded as a further donor atom, while on the other hand the corresponding nitrogen atom of the peptidic chelator "—NNNC—" is involved in a further peptide bond and hence does not constitute a further donor atom:

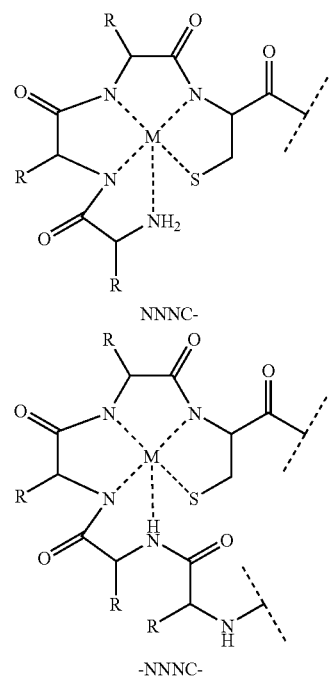

NNNC-

-NNNC-

Preferably, the stabilizing sidechain has a structure represented by a formula selected from the group consisting of formulas (IV a), (IV b), (IV c) and (IV d):

$$—(Y^1)_n\text{-D} \quad \text{(IV a)}$$

$$—(Y^1)_{n-1}—Y^2\text{-D} \quad \text{(IV b)}$$

$$—Y^3—(Y^1)_{n-1}\text{-D} \quad \text{(IV c)}$$

$$Y^3—Y^2—(Y^1)_{n-2}\text{-D} \quad \text{(IV d)}$$

wherein
n is 2 or 3;
$Y^1$ is —C(R$^{15}$R$^{16}$)—, —NR$^{17}$—, —O—, or —S—;
$Y^2$ is —C(R$^{18}$R$^{19}$)—, —NR$^{20}$—, —O—, or —S—;
$Y^3$ is —C(R$^{21}$R$^{22}$)—, —NR$^{23}$—, —O—, or —S—;
D is —NR$^{24}$R$^{25}$, —OR$^{26}$, —SR$^{26}$, or —PR$^{27}$R$^{28}$;
wherein
R$^{15}$ and R$^{16}$ are independently —H, —OH, —CO$_2$H, —C$_1$-C$_6$-alkyl, —C$_1$-C$_4$-alkyl, —OH—CO—C$_1$-C$_6$-alkyl, or R$^{15}$ and R$^{16}$ together with the carbon atom to which they are attached form a carbonyl group or an imino group;
R$^{17}$ is —H, —OH, —C$_1$-C$_6$-alkyl, —C$_1$-C$_4$-alkyl-OH, or —CO—C$_1$-C$_6$-alkyl;
R$^{18}$ and R$^{19}$ are independently —H, —OH, —CO$_2$H, —C$_1$-C$_6$-alkyl, —C$_1$-C$_4$-alkyl-OH, —CO—C$_1$-C$_6$-alkyl, or R$^{18}$ and R$^{19}$ together with the carbon atom to which they are attached form a carbonyl group;
R$^{20}$ is is —H, —OH, —C$_1$-C$_6$-alkyl, —C$_1$-C$_4$-alkyl-OH, or —CO—C$_1$-C$_6$-alkyl;
R$^{21}$ and R$^{22}$ are independently —H, —OH, —CO$_2$H, —C$_1$-C$_6$-alkyl, —C$_1$-C$_4$-alkyl-OH, —CO—C$_1$-C$_6$-alkyl, or R$^{21}$ and R$^{22}$ together with the carbon atom to which they are attached form a carbonyl group;
R$^{23}$ is —H, —OH, —C$_1$-C$_6$-alkyl, —C$_1$-C$_4$-alkyl-OH, or —CO—C$_1$-C$_6$-alkyl;

$R^{24}$ and $R^{25}$ are independently —H, —OH, —$C_1$-$C_6$-alkyl, —$C_1$-$C_4$-alkyl-OH, —CO—$C_1$-$C_6$-alkyl, —C($NH_2$)=$NH_2$, or —$CONH_2$;

$R^{26}$ is —H, —$C_1$-$C_6$-alkyl, —$C_1$-$C_4$-alkyl-OH, or —CO—$C_1$-$C_6$-alkyl, or $R^{15}$ or $R^{17}$ together with $R^{18}$, $R^{20}$, $R^{21}$, or $R^{23}$ form a 4 to 6 membered saturated or unsaturated ring; or $R^{18}$ or $R^{20}$ together with $R^{24}$ or $R^{26}$ form a 4 to 6 membered saturated or unsaturated ring containing 1 to 4 heteroatoms independently selected from the group consisting of N, O and S; and $R^{27}$ and $R^{28}$ are independently —H, —OH, —$C_1$-$C_6$-alkyl, —$C_1$-$C_6$-alkyl-$CO_2H$, —$C_1$-$C_4$-alkyl-OH, or —O—$C_1$-$C_6$-alkyl.

Preferably, those embodiments are excluded from the definition of formulas (IV a), (IV b), (IV c) and (IV d), in which (i) an oxygen atom is covalently bound to a nitrogen atom, a sulfur atom or another oxygen atom, (ii) a sulfur atom is covalently bound to a nitrogen atom or another sulfur atom, (iii) a nitrogen atom is covalently bound to another nitrogen atom, or (iv) a carbonyl carbon is covalently bound to another carbonyl carbon.

More preferably, the stabilizing sidechain has the structure represented by a formula selected from the group consisting of formulas (IV a), (IV b) and (IV c) as defined above, wherein $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently —H, —$C_1$-$C_6$-alkyl, or —$C_1$-$C_6$-alkyl-OH, and $R^{15}$ or $R^{17}$ together with $R^{18}$, $R^{20}$, $R^{21}$, or $R^{23}$ may form a 4 to 6 membered saturated or unsaturated ring; or $R^{18}$ or $R^{20}$ together with $R^{24}$ or $R^{26}$ may form a 4 to 6 membered saturated or unsaturated ring containing 1 to 4 heteroatoms independently selected from the group consisting of N, O and S; and $R^{27}$ and $R^{28}$ are independently —H, —$C_1$-$C_6$-alkyl or —O—$C_1$-$C_6$-alkyl.

Most preferably, the stabilizing sidechain has a structure represented by a formula selected from the group consisting of formulas (IV a), (IV b) and (IV c) as defined above, wherein n is 2 or 3; $Y^1$ is —C($R^{15}R^{16}$)—; $Y^2$ is —C($R^{18}R^{19}$)—; $Y^3$ is —C($R^{21}R^{22}$)—; and D is —$NR^{24}R^{25}$, —$OR^{26}$ or —$SR^{26}$;

wherein $R^{15}$ and $R^{16}$ are —H; $R^{18}$ and $R^{19}$ are —H; or $R^{18}$ and $R^{19}$ together with the carbon atom to which they are attached form a carbonyl group; $R^{21}$ and $R^{22}$ together with the carbon atom to which they are attached form a carbonyl group;

$R^{24}$ and $R^{25}$ are —H; $R^{26}$ is —H or —$C_1$-$C_6$-alkyl; or $R^{18}$ together with $R^{24}$ forms a 4 to 6 membered saturated or unsaturated ring containing 2 or 3 heteroatoms independently selected from the group consisting of N, O and S.

Preferred examples of the stabilizing sidechain are:

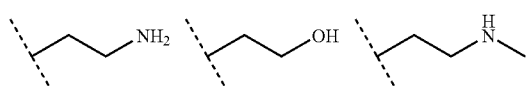

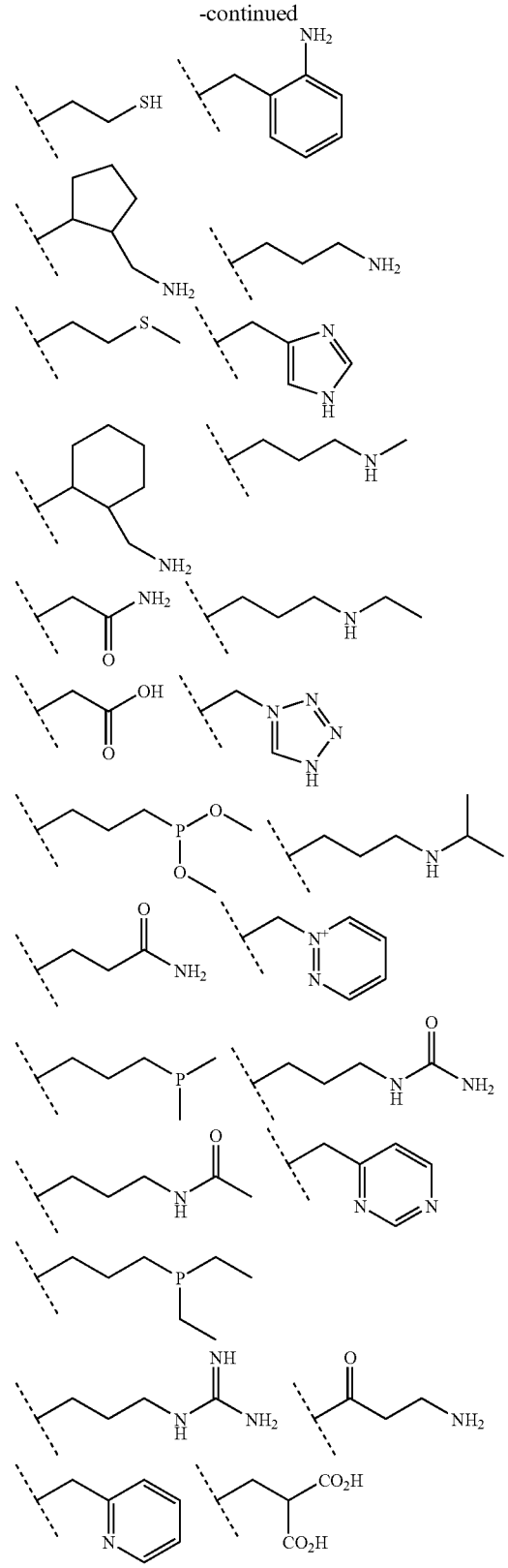

More preferably the stabilizing sidechain is a moiety selected from the group consisting of —$CH_2CH_2NH_2$, —$CH_2CH_2CH_2NH_2$, —$CH_2CH_2CONH_2$, —CH$_2$CH$_2$COOH, —COCH$_2$CH$_2$NH$_2$, —CH$_2$CH$_2$—S—CH$_3$, —CH$_2$CH$_2$CH$_2$NHC(NH)NH$_2$, —CH$_2$CH$_2$CH$_2$NHCONH$_2$, —CH$_2$CH(CO$_2$H)$_2$, and —CH$_2$-(4-imidazolyl). Most preferably, the sidechain is selected from —CH$_2$CH$_2$CH$_2$NH$_2$, —CH$_2$CH$_2$CONH$_2$, —CH$_2$CH$_2$COOH, —CH$_2$CH$_2$—S—CH$_3$, —CH$_2$CH$_2$CH$_2$NHC(NH)NH$_2$, and —CH$_2$-(4-imidazolyl), i.e. the sidechain belongs to an α-amino acid selected from Orn, Gln, Glu, Met, Arg and His, respectively.

If the stabilizing sidechain is the sidechain of the amino acid Orn, this amino acid preferably is D-Orn.

In a preferred embodiment the stabilizing sidechain does not contain a tertiary amine.

If the targeting moiety is a cyclic somatostatin derivative or cyclic somatostatin receptor binding peptide, then the stabilizing side chain is not —CH$_2$CH$_2$CH$_2$NH$_2$, —CH$_2$CH$_2$NH$_2$, —CH$_2$-(4-imidazolyl), or —CH$_2$CH$_2$CH$_2$NHC(NH)NH$_2$, and if the targeting moiety is folate or folic acid or an analog thereof, then the stabilizing side chain is not —CH$_2$COOH. Preferably, if the targeting moiety is a cyclic peptide, the cyclic peptide is not a cyclic somatostatin derivative or cyclic somatostatin receptor binding peptide.

In a preferred embodiment peptide P does not contain amino acid residues derived from β-homo amino acids, cyclic amino acids or N-methyl amino acids.

The peptide P of the invention comprises a radioactive metal complexed to the complexing amino acid sequence. Preferably, peptide P contains a radioactive metal which is selected from the group consisting of $^{46}$Sc, $^{47}$Sc, $^{60}$Cu, $^{62}$Cu, $^{64}$Cu, $^{67}$Cu, $^{66}$Ga, $^{67}$Ga, $^{68}$Ga, $^{86}$Y, $^{90}$Y, $^{94m}$Tc, $^{99}$Tc, $^{99m}$Tc, $^{105}$Rh, $^{103}$Pd, $^{111}$In, $^{142}$Pr, $^{149}$Pm, $^{153}$Sm, $^{159}$Gd, $^{166}$Ho, $^{177}$Lu, $^{186}$Re, $^{188}$Re, $^{199}$Pt, $^{213}$Bi, $^{225}$Ac, $^{52}$Fe, $^{62}$Zn, $^{89}$Zr, $^{103}$Ru, $^{161}$Tb, and $^{117m}$Sn. More preferably, the radioactive metal is selected from the group consisting of $^{60}$Cu, $^{62}$Cu, $^{64}$Cu, $^{67}$Cu, $^{94m}$Tc, $^{99}$Tc, $^{99m}$Tc, $^{103}$Pd, $^{186}$Re, $^{188}$Re and $^{199}$Pt. Preferably, $^{99m}$Tc, $^{186}$Re, or $^{188}$Re are complexed to the planar chelator in the form of oxotechnetium and oxorhenium, respectively.

Labeling with $^{99m}$Tc is an advantage because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other imaging radionuclides known in the prior art have effective half-lives that are much longer (for example, $^{111}$In, which has a half life of 67.4 h) and therefore must be handled longer for proper radioactive waste decay and disposal, or pose a risk for contamination because they can react to form volatile species (for example, $^{123}$I). Both $^{186}$Re and $^{188}$Re are β-emitters and thus are suitable for therapeutic applications. $^{186}$Re additionally emits a γ-ray at essentially the same energy as the γ emission of $^{99m}$Tc, allowing monitoring of biodistribution using the same instrumentation as is used for $^{99m}$Tc imaging. $^{188}$Re is available as a no carrier added isotope from a $^{188}$W/$^{188}$Re generator analogous to the $^{99}$Mo-$^{99m}$Tc generator. Those of skill will recognize that the chemical properties of technetium and rhenium are similar or substantially the same, as described in Deutsch, et al. (1986), Nucl. Med. Biol. 13, 465-477.

The invention also relates to a compound PG comprising
(a) the peptide P as defined above and
(b) a functional group G capable of reacting with a targeting moiety T,
wherein the functional group G is selected from the group consisting of carboxyl (—CO$_2$H), activated carboxyl, amino (—NH$_2$), aldehyde (—CHO), hydrazine (—NHNH$_2$), semicabacide (—NHCONHNH$_2$), thiosemicarbacide (—NHCSNHNH$_2$), isocyanate (—NCO), isothiocyanate (—NCS), imino esters (—OCNH—), maleine imide, alkenyl (—CH=CH$_2$), alkenylene (—CH=CH—), dienyl (—CH=CH—CH=CH$_2$), dienylene (—CH=CH—CH=CH—), alkynyl (—C≡CH), alkynylene (—C≡C—), α-halocarbonyl (—CO-hal), halosulfonyl (—SO$_2$-hal), haloacetamide (—NH—CO—CH$_2$-hal), acylamino (—NHCO—), mixed anhydride (—CO—O—CO—), azide (—N$_3$), hydroxy (—OH), carbodiimide (—N=C=N—), α,β-unsaturated carbonyl (—CH=CH—CO—) and haloacetyl (—CO—CH$_2$-hal), wherein halo means fluoro, chloro, bromo or iodo.

For the purpose of the specification "activated carboxyl" means a carboxyl group which is derivatised in order to facilitate the reaction with a nucleophilic group. Suitable activating groups are known to the person of ordinary skill and in this regard it can be referred to e.g. M. A. Bodanszky, "The Practice of Peptide Synthesis", Springer 1984. Examples are adducts of carboxylic acids with carbodiimides or activated esters, such as esters of hydroxybenzotriazole. Particularly preferred are activated carboxyl groups selected from the group consisting of esters of 4-nitrophenol, 3,5-dinitrophenol, pentafluorophenol, N-hydroxy-succinimide and hydroxybenzotriazole.

The invention also relates to to a conjugate PGT comprising a compound PG as defined above and a targeting moiety T, wherein the targeting moiety T is covalently linked to the compound PG through a functional group G as defined above.

The targeting moiety T comprises a structural motif capable of selectively recognizing and binding to specific targets in a mammalian body.

Preferably the targeting moiety T is not connected to the complexing amino acid sequence of the peptide P via the stabilizing sidechain.

In a preferred embodiment the targeting moiety T is a molecule selected from the group consisting of polyacetals (e.g. polysaccharides), oligoacetals (e.g. oligosaccharides), polyesters (e.g. polynucleotides), oligoesters (e.g. oligonucleotides), polyamides (e.g. proteins), oligoamides (e.g. peptides), polyolefins (e.g. polyisoprenoids), oligoolefins (e.g. terpenes, steroids), glycoproteins, lipoproteins, antibodies, glycanes, vector amines, biogene amines, pharmaceutical drugs (e.g. antibiotics), bioactive lipids, lipoids, fatty acid esters, triglycerides, liposomes, porphyrins, texaphrins, cytochrome, inhibitors, neuramidases, prostaglandins, endothelines, alkaloids, vitamins and their analogues, hormons, antihormons, DNA-intercalators, nucleosides, nucleotides, lektins, peptides, antibody fragments, camelids, diabodies, minibodies, receptor agonists, receptor antagonists, and aptamers.

Preferably, the targeting moiety T comprises a targeting amino acid sequence and the conjugate PT or the conjugate PGT in total comprises at least 7 but not more than 500 amino acid residues, more preferably not more than 250, still more preferably not more than 100, most preferably not more than 50, in particular not more than 25 amino acid residues.

Preferably, the targeting moiety T has a molecular weight within the range of from 50 to 180,000 gmol$^{-1}$, more preferably from 100 to 80,000 gmol$^{-1}$, still more preferably from 200 to 40,000 gmol$^{-1}$, most preferably from 300 to 10,000 gmol$^{-1}$.

Preferably, the conjugate PT or the conjugate PGT has a molecular weight within the range of from 300 to 200,000 gmol$^{-1}$, more preferably from 500 to 100,000 gmol$^{-1}$, still more preferably from 700 to 50,000 gmol$^{-1}$, most preferably from 800 to 12,000 gmol$^{-1}$.

Preferably, the targeting moiety T is a molecule which occurs in vivo in an organism or which can be synthesized in vitro. In principle, the targeting moiety T is capable of interacting with a target, preferably with another molecule or molecular structure which occurs in vivo in an organism. Preferably, said interaction between the targeting moiety T and its target is based on molecular recognition resulting in a selective binding. Preferably, the binding is effected by hydrophobical interactions and/or hydrogen bonding.

Preferably, the targeting moiety T is capable of binding, preferably selectively binding to a cell surface receptor.

Preferably, the $K_D$ value of the targeting moiety T and its target is <100 µM, more preferably <10 µM, still more preferably <1 µM, most preferably <100 nM, in particular <10 nM. The skilled person is aware of suitable methods for determining the $K_D$ value of a given set of target and tageting moiety T under standard conditions by routine experimentation. Regarding details it can be referred to e.g. H. E. Junginger "Drug Targeting and Delivery: Concepts in Dosage Form Design", T&F STM, 1993; H. Schreier "Drug Targeting Technology: Physical, Chemical and Biological Methods", $1^{st}$ ed, Marcel Dekker 2001; A. M. Hillery et al., "Drug Delivery and Targeting: For Pharmacists and Pharmaceutical Scientists", $1^{st}$ ed, T&F STM, 2002 the disclosure of which being incorporated by reference herein.

In one embodiment the targeting moiety T does not comprise amino acid residues.

In another embodiment, however, the targeting moiety T comprises a targeting amino acid sequence. This embodiment will be further described in the following.

Preferably, the targeting moiety T comprises a targeting amino acid sequence selected from the group consisting of somatostatin receptor binding peptides, cyclic GPIIb/IIIa receptor binding peptides, leukocyte binding peptides, peptides derived from platelet factor 4, vasoactive intestinal peptide receptor binding peptides, neuropeptide Y receptor binding peptides, alpha-melanocyte-stimulating hormone receptor binding peptides, neurotensin receptor binding peptides, urokinase plasminogen activator receptor binding peptides, gastrin releasing peptide receptor binding peptides, $\alpha(v)\beta(3)$ receptor binding peptides, cholecystokinin receptor binding peptides, calcitonin receptor binding peptides, and chemotactic peptides.

When the targeting moiety T of the conjugate PT or the conjugate PGT comprises a targeting amino acid sequence, a given amino acid residue may be incorporated e.g.

either in the complexing amino acid sequence of the peptide P, or optionally in the remainder of the peptide P, or in the targeting amino acid sequence of the targeting moiety T, or optionally in the remainder of the targeting moiety T.

In that case the conjugate PT or the conjugate PGT are comprised of only amino acid residues and/or single thiol moieties linked by amide bonds, the conjugates can alternatively be regarded as a peptide P' containing at least 7 but not more than 500 amino acid residues including a complexing amino acid sequence as defined above and a targeting amino acid sequence as defined above. Thus, under these circumstances it does not make a difference whether a given amino acid residue among the 7 to 500 amino acid residues of the conjugate (peptide P') belongs e.g. to the remainder of the peptide P or the remainder of the targeting moiety T, as long as the overall conjugate (peptide P') contains a complexing amino acid sequence, a targeting amino acid sequence and at least 7 but not more than 500 amino acid residues.

In general when T is a targeting amino acid sequence, the complexing amino acid sequence and the targeting amino acid sequence may be covalently linked with bonds other than amide bonds. They may be covalently linked directly with one another or through the peptide backbone of a further amino acid sequence (linking amino acid sequence). However, the covalent linkage may also be effected through the sidechain of a given amino acid residue contained in the complexing amino acid sequence and the sidechain of another amino acid residue contained in the targeting amino acid sequence. Alternatively, the sidechain of an amino acid residue contained in the first amino acid sequence (complexing or targeting amino acid sequence) may be covalently linked to the N-terminus or the C-terminus of the other amino acid sequence, respectively.

In a preferred embodiment the complexing amino acid sequence is covalently linked to a sulfur-containing sidechain of the targeting amino acid sequence through the moiety —CH$_2$CO—. For example the moiety —(N-Me)Hcy-CH$_2$CO($\beta$)Dap-, wherein "(N-Me)Hcy" is part of the targeting amino acid sequence and stands for N-methyl-homocysteine and "($\beta$)Dap" is part of the complexing amino acid sequence and stands for $\beta$-diaminopropionic acid; —(N-Me)Hcy-CH$_2$CO($\beta$)Dap- has the following structure:

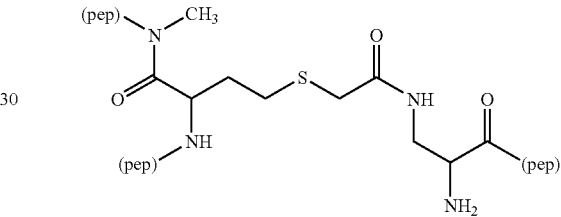

The invention also relates to a pharmaceutical composition comprising a conjugate PT or a conjugate PGT as defined above and a pharmaceutically acceptable carrier.

The invention also relates to a pharmaceutical composition comprising the conjugate PT or the conjugate PGT together with a pharmaceutically acceptable carrier. The radioactively labeled conjugates provided by the invention may be administered intravenously in any pharmaceutically acceptable carrier, e.g. conventional medium such as an aqueous saline medium, or in blood plasma medium, as a pharmaceutical composition for intravenous injection. Such medium may also contain conventional pharmaceutical adjunct materials such as, for example, pharmaceutically acceptable salts to adjust the osmotic pressure, buffers, preservatives and the like. Among the preferred media are normal saline and plasma. Suitable pharmaceutical acceptable carriers are known to the person skilled in the art. In this regard it can be referred to e.g. Remington's Practice of Pharmacy, $11^{th}$ ed.

The concentration of the conjugates and the pharmaceutically acceptable carrier, for example, in an aqueous medium, varies with the particular field of use. A sufficient amount is present in the pharmaceutically acceptable carrier when satisfactory visualization of the imaging target (e.g. a tumor) is achievable or therapeutic results are achievable.

The peptides and conjugates according to the invention can be chemically synthesized in vitro. The peptides P can generally advantageously be prepared on an amino acid synthesizer. Preferably, particularly when the targeting moiety T comprises a targeting amino acid sequence, the peptides may be synthesized sequentially, i.e. the complexing amino acid sequence (and optionally the targeting amino acid sequence)

may be obtained by subsequently adding suitable activated and protected amino acid derivatives to the growing amino acid chain. For details regarding peptide synthesis it can be referred to e.g. B. Gutte "Peptides: Synthesis, Structures, and Applications", Academic Press, 1995; X. C. Chan et al. "Fmoc Solid Phase Peptide Synthesis: A Practical Approach", Oxford University Press, 2000; J. Jones "Amino Acid and Peptide Synthesis", $2^{nd}$ ed., Oxford University Press, 2002; M. Bodanszky et al., "Principles of Peptide Synthesis", $2^{nd}$ ed., Springer, 1993.

In another embodiment, the peptide P and the targeting moiety T are synthesized separately. Subsequently, the peptide P is covalently linked to the targeting moiety T during chemical in vitro synthesis, using techniques well known to those with skill in the art.

In a preferred embodiment a compound PG bearing a functional group G as defined above is ligated with a targeting moiety T bearing a complementary functional group which is capable of selectively reacting with the functional group G thereby yielding a conjugate PGT. For example, a maleimido group (functional group G) of a compound PG may selectively react with a thiol group (complementary functional group) of the targeting moiety, or vice versa.

In forming a complex of radioactive technetium or rhenium with the amino acid sequence to be complexed, the technetium or rhenium starting material, preferably a salt of $^{99m}$Tc pertechneate, $^{186}$Re perrhenate, or $^{188}$Re perrhenate, is reacted with the amino acid sequence in the presence of a reducing agent; in a preferred embodiment, the reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of the molecule comprising the amino acid sequence that is to be labeled and a sufficient amount of reducing agent to label the sequence with $^{99m}$Tc, $^{186}$Re, or $^{188}$Re. Alternatively, the complex may be formed by reacting the amino acid sequence with a pre-formed labile complex of technetium or rhenium and another compound known as a transfer ligand. This process is known as ligand exchange and is well known to those skilled in the art. The labile complex may be formed using such transfer ligands as tartrate, citrate, gluconate, glucoheptonate or mannitol, for example. Among the $^{99m}$Tc pertechneate, $^{186}$Re perrhenate, or $^{188}$Re perrhenate salts useful with the invention are included the alkali metal salts such as the sodium salt, or ammonium salts or $C_1$-$C_6$-alkyl ammonium salts. The reaction of the amino acid sequence with technetium pertechneate or rhenium perrhenate or preformed $^{99m}$Tc, $^{186}$Re, or $^{188}$Re labile complex can be carried out in an aqueous medium at room temperature or with heating up to 100° C. If the metal complex has an anionic charge, it is formed in the aqueous medium in the form of a salt with a suitable cation such as sodium cation, ammonium cation, mono, di or tri $C_1$-$C_6$-alkyl amine cation, etc. Any conventional salt of the anionic complex with a pharmaceutically acceptable cation can be used in accordance with this invention.

In another embodiment of the invention as related to technetium and rhenium labeling, a free thiol on the amino acid sequence to be complexed can be made available (e.g. a disulfide bond is broken, or a thiol protecting group is removed) by reduction of the amino acid sequence prior to labeling. In a preferred embodiment, the reducing agent is stannous chloride. In an additional preferred embodiment, the reducing agent is a solid-phase reducing agent. The pre-reduced amino acid sequence is then labeled by reaction with $^{99m}$Tc, $^{186}$Re, or $^{188}$Re under reducing conditions or with pre-reduced $^{99m}$Tc, $^{186}$Re, or $^{188}$Re or a $^{99m}$Tc, $^{186}$Re, or $^{188}$Re complex.

Radioactively labeled peptides and conjugates provided by the invention have a suitable amount of radioactivity. In forming $^{99m}$Tc, $^{186}$Re, or $^{188}$Re radioactive complexes, it is generally preferred to form radioactive complexes in solutions containing radioactivity at concentrations of from about 0.1 millicurie (mCi) to 300 mCi per ml.

Technetium-labeled conjugates provided by the invention can be used for visualizing organs such as the kidney, heart or brain, for diagnosing disorders in these organs, and tumors, such as gastrointestinal tumors, myelomas and small cell lung carcinoma, endocrine tumors such as medullary thyroid carcinomas and pituitary tumors, brain tumors such as meningiomas and astrocytomas, and tumors of the prostate, breast, colon, and ovaries can also be imaged. The conjugates of the invention are also used to image disease states such as thromboses, atherosclerosis, and the like. The site imaged by the conjugates of the invention will be determined by the binding specificity of the targeting moiety, e.g. the targeting amino acid sequence. Conjugates of the invention labeled with therapy isotopes (e.g. $^{186}$Re, $^{188}$Re, $^{64}$Cu, etc.) may be used particularly for treatment of tumors bearing the site targeted by the targeting moiety of the conjugates of the invention.

In accordance with the invention, the ratiolabeled conjugates either as a neutral complex or as a salt with a pharmaceutically acceptable counterion are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with the invention. Generally, the unit dose to be administered for a diagnostic agent has a radioactivity of about 0.1 mCi to about 100 mCi, preferably 1 mCi to 20 mCi. For a radiotherapeutic agent, the radioactivity of the therapeutic unit dose is about 10 mCi to 700 mCi, preferably 50 mCi to 400 mCi. The solution to be injected at unit dosage is from about 0.01 ml to about 30 ml. For diagnostic purposes after intravenous administration, imaging of the organ or tumor in vivo can take place in a matter of a few minutes. However, imaging takes place, if desired, in hours or even longer, after injecting into patients. In most instances, a sufficient amount of the administered dose will accumulate in the area to be imaged within about 0.1 of an hour to permit the taking of scintigraphic images. Any conventional method of scintigraphic imaging for diagnostic purposes can be utilized in accordance with this invention.

The invention also relates to the use of a stabilizing sidechain for increasing the thermodynamic stability of a complex formed between (a) a tridentate or tetradentate planar chelator containing a ligand backbone defined by a perimeter containing (i) three or four donor atoms and (ii) intervening atoms between the donor atoms (b) and a radioactive metal, wherein the stabilizing sidechain comprises a further donor atom covalently linked to the ligand backbone of the planar chelator through two or three intervening atoms.

Regarding the terms "stabilizing sidechain", "planar chelator", "ligand backbone", "donor atom", "intervening atom", "radioactive metal" etc. it is referred to the definitions and preferred embodiments specified above.

A preferred embodiment of the invention relates to the use of a stabilizing sidechain for stabilizing a metal complex, the stabilizing sidechain being covalently linked through a single bond to the ligand backbone of a planar tridentate or tetradentate chelator, wherein the stabilizing sidechain has a structure represented by a formula selected from the group consisting of formulas (IV a), (IV b), (IV c) and (IV d):

$$—(Y^1)_n\text{-}D \quad \text{(IV a)}$$

$$—(Y^1)_{n-1}—Y^2\text{-}D \quad \text{(IV b)}$$

$$—Y^3—(Y^1)_{n-1}\text{-}D \quad \text{(IV c)}$$

$$—Y^3—Y^2—(Y^1)_{n-2}\text{-}D \quad \text{(IV d)}$$

wherein n is 2 or 3;

$Y^1$ is $—C(R^{15}R^{16})—$, $—NR^{17}—$, $—O—$, or $—S—$;

$Y^2$ is $—C(R^{18}R^{19})—$, $—NR^{20}—$, $—O—$, or $—S—$;

$Y^3$ is $—C(R^{21}R^{22})—$, $—NR^{23}—$, $—O—$, or $—S—$;

D is $—NR^{24}R^{25}$, $—OR^{26}$, $—SR^{26}$, or $—PR^{27}R^{28}$;

wherein $R^{15}$ and $R^{16}$ are independently $—H$, $—OH$, $—CO_2H$, $—C_1\text{-}C_6\text{-alkyl}$, $—C_1\text{-}C_4\text{-alkyl-OH}$, $—CO—C_1\text{-}C_6\text{-alkyl}$, or $R^{15}$ and $R^{16}$ together with the carbon atom to which they are attached form a carbonyl group or an imino group;

$R^{17}$ is $—H$, $—OH$, $—C_1\text{-}C_6\text{-alkyl}$, $—C_1\text{-}C_4\text{-alkyl-OH}$, or $—CO—C_1\text{-}C_6\text{-alkyl}$;

$R^{18}$ and $R^{19}$ are independently $—H$, $—OH$, $—CO_2H$, $—C_1\text{-}C_6\text{-alkyl}$, $—C_1\text{-}C_4\text{-alkyl-OH}$, $—CO—C_1\text{-}C_6\text{-alkyl}$, or $R^{18}$ and $R^{19}$ together with the carbon atom to which they are attached form a carbonyl group;

$R^{20}$ is is $—H$, $—OH$, $—C_1\text{-}C_6\text{-alkyl}$, $—C_1\text{-}C_4\text{-alkyl-OH}$, or $—CO—C_1\text{-}C_6\text{-alkyl}$, $R^{21}$ and $R^{22}$ are independently $—H$, $—OH$, $—CO_2H$, $—C_1\text{-}C_6\text{-alkyl}$, $—C_1\text{-}C_4\text{-alkyl-OH}$, $—CO—C_1\text{-}C_6\text{-alkyl}$, or $R^{21}$ and $R^{22}$ together with the carbon atom to which they are attached form a carbonyl group;

$R^{23}$ is $—H$, $—OH$, $—C_1\text{-}C_6\text{-alkyl}$, $—C_1\text{-}C_4\text{-alkyl-OH}$, $—CO—C_1\text{-}C_6\text{-alkyl}$;

$R^{24}$ and $R^{25}$ are independently $—H$, $—OH$, $—C_1\text{-}C_6\text{-alkyl}$, $—C_1\text{-}C_4\text{-alkyl-OH}$, $—CO—C_1\text{-}C_6\text{-alkyl}$, $—C(NH_2)=NH_2$, or $—CONH_2$;

$R^{26}$ is $—H$, $—C_1\text{-}C_6\text{-alkyl}$, $—C_1\text{-}C_4\text{-alkyl-OH}$, $—CO—C_1\text{-}C_6\text{-alkyl}$; or $R^{15}$ or $R^{17}$ together with $R^{18}$, $R^{20}$, $R^{21}$, or $R^{23}$ form a 4 to 6 membered saturated or unsaturated ring; or $R^{18}$ or $R^{20}$ together with $R^{24}$ or $R^{26}$ form a 4 to 6 membered saturated or unsaturated ring containing 1 to 4 heteroatoms independently selected from the group consisting of N, O and S; and $R^{27}$ and $R^{28}$ are independently $—H$, $—OH$, $—C_1\text{-}C_6\text{-alkyl}$, $—C_1\text{-}C_6\text{-alkyl-}CO_2H$, $—C_1\text{-}C_4\text{-alkyl-OH}$, or $—O—C_1\text{-}C_6\text{-alkyl}$, wherein the ligand backbone is defined by the 3 or 4 donor atoms of the tridentate or tetratdentate chelator, and the intervening atoms between them;

and wherein the planar chelator (a) is a complexing amino acid sequence with a single thiol moiety having a structure represented by general formula (I)

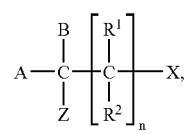

wherein

A is $—CO_2H$, $—CONH_2$, $—CO_2\text{-(pep)}$, $—CONH\text{-(pep)}$, or $R^4$;

B is $—SH$, $—NHR^3$, $—N(R^3)\text{-(pep)}$, or $R^4$;

X is $—SH$, $—NHR^3$, $—N(R^3)\text{-(pep)}$, or $R^4$;

Z is $—H$ or $—CH_3$;

n is 0, 1, or 2;

$R^1$, $R^2$, $R^3$, and $R^4$ are independently $—H$ or $—C_1\text{-}C_6\text{-alkyl}$;

(pep) represents the remainder of the complexing amino acid sequence, respectively;

provided that either (a) B is $—NHR^3$ or $—N(R^3)\text{-(pep)}$; X is $—SH$; and n is 1 or 2; or (b) B is $—SH$; X is $—NHR^3$ or $—N(R^3)\text{-(pep)}$; and n is 1 or 2; or (c) A is $—CO_2\text{-(pep)}$ or $—CONH\text{-(pep)}$; B is $R^4$; X is $—SH$ and n is 0 or 1; or (d) A is $R^4$; B is $—SH$; and X is $—N(R^3)\text{-(pep)}$; or (e) A is $R^4$; B is $—N(R^3)\text{-(pep)}$; and X is $—SH$; or (f) A is $—CO_2\text{-(pep)}$ or $—CONH\text{-(pep)}$; B is $—SH$; and X is $R^4$; or (g) A is $—CO_2\text{-(pep)}$ or $—CONH\text{-(pep)}$; B is $—SH$; X is $—CH_3$; Z is $—CH_3$; and n is 0;

and provided that at least one moiety (pep) is present.

or (b) has the structure of general formula (V)

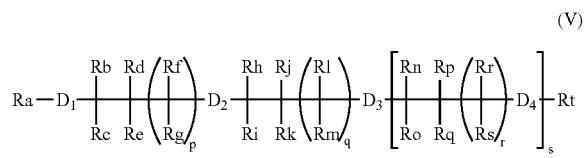

wherein $D_1$, $D_2$, $D_3$ and $D_4$ are independently $—NH—$, $—NRu—$, or $—S—$;

Ra and Rt are independently $—H$, $—C_1\text{-}C_6\text{-alkyl}$ which may optionally be substituted, $—Rx$, or a suitable nitrogen or sulfur protecting group.

Rb to Ru are independently $—H$, $—C_1\text{-}C_6\text{-alkyl}$ which may be substituted, $—CO_2H$, $—OH$ or $—Rx$; or Rb with Rc, Rd with Re, Rf with Rg, Rh with Ri, Rj with Rk, Rl with Rm, Rn with Ro, Rp with Rq, and Rr with Rs together with the carbon atom to which they are attached may independently form a carbonyl group;

any two adjacent C or N atoms in the ligand backbone along with attached R groups may independently form C=C or C=N double bonds;

Rx is a linker moiety and p, q, r, and s are independently 0 or 1.

Preferably, in the definition of formulas (IV a), (IV b), (IV c) and (IV d) those embodiments are excluded, in which
(i) an oxygen atom is covalently bound to a nitrogen atom, a sulfur atom or another oxygen atom,
(ii) a sulfur atom is covalently bound to a nitrogen atom or another sulfur atom, or
(iii) a nitrogen atom is covalently bound to another nitrogen atom.

Preferred examples of planar chelators having the structure of general formula (V) are:

DADS

DADT or BAT

MAMA

EC

MAG2

PnAO

AADT

GlyGlyCys (N-Me$_2$)GlySerCys

Preferably, the chelators (e.g. the peptide P) of the invention exhibit a thermodynamic stability such that in aqueous solution after 8 hours more than 75% of the initial radioactive metal are still complexed, more preferably more than 80%0, still more preferably more than 85%, most preferably more than 87.5%, in particular more than 90% are still complexed. The percentage of complexation can be monitored by HPLC under the conditions as further described in Example 3.

Figure 1:
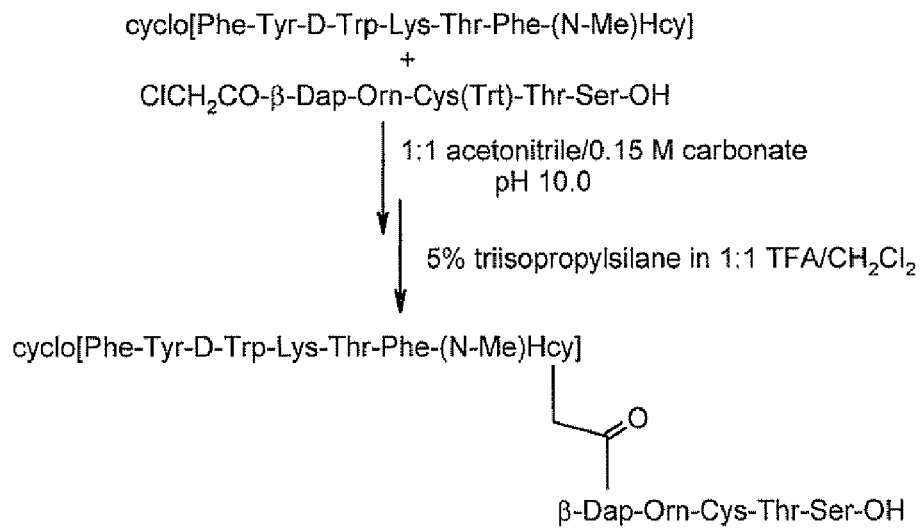
FIG. 1 shows a typical procedure for coupling and final deprotection steps of a synthesis for the invention.

The following examples further illustrate the subject matter of the invention but should not be construed as limiting its scope.

EXAMPLE 1

Solid Phase Peptide Synthesis of Model Chelator Peptides

Solid phase peptide synthesis (SPPS) was carried out on a 0.1-0.25 millimole scale on an automated peptide synthesizer using 9-fluorenylmethyloxycarbonyl (Fmoc) amino-terminus protection, coupling with O-(benzotriazol-1-yl)-N,N,N',N'-bis(pentmethylene)uronium tetra-fluoroborate/hydroxybenzotriazole or dicyclohexylcarbodiimide/hydroxybenzotriazole (TBTU/HOBT or HBTU/HOBT), and using Rink amide resin for carboxyl-terminus amides. N-terminal acetyl groups, benzoyl groups, or mercaptoacetyl groups were introduced by using acetic acid, benzoic acid, or mercaptoacetic acid, respectively, as the last residue coupled during SPPS.

Where appropriate, the following method was used to introduce acyl groups to the α-amino group of a diaminopropionic (Dap) moiety: The peptide was synthesized by SPPS using diaminopropionic acid protected at the α-amine position with allyloxycarbonyl. The alloxycarbonyl protecting group was removed using $Pd(PPh_3)_2$ in the presence of triphenylsilane and activated t-butoxycarbonyl-β-alanine was coupled at the free amine group.

Resin-bound products were routinely cleaved using a solution comprised of trifluoroacetic acid, water, thioanisole, ethanedithiol, and triethylsilane, prepared in ratios of 100:5:5:2.5:2 for 1.5-3 hours at room temperature. Crude peptides were purified by preparative reversed phase high pressure liquid chromatography (HPLC) using gradient elution with 0.1% trifluoroacetic acid (TFA) in water modified with acetonitrile. Acetonitrile was evaporated from the eluted fractions which were then lyophilized. The purities of the peptides were ≧90% by reversed phase HPLC. The identity of each product was confirmed by fast atom bombardment mass spectrometry (FABMS) or elctro spray ionization mass spectrometry (ESI-MS).

Table 1 presents peptides prepared according to Example 1 along with MS results. All amino acids are in the L-form unless specified as D.

TABLE 1

| Compound | MS: $M + H^+$ | $M_w$ calcd |
|---|---|---|
| Bz-Gly-Gly-Gly-Cys-Ala.amide (SEQ ID NO: 1) | 467 | 466.5 |
| Bz-Gly-Gly-Met-Cys-Ala.amide (SEQ ID NO: 2) | 541 | 540.6 |
| Bz-Gly-Gly-Orn-Cys-Ala.amide (SEQ ID NO: 3) | 524 | 523.6 |
| Bz-Gly-Gly-(D)Orn-Cys-Ala.amide | 524 | 523.6 |
| Bz-Gly-Orn-Gly-Cys-Ala.amide (SEQ ID NO: 4) | 524 | 523.6 |
| Bz-Gly-Gly-Gln-Cys-Ala.amide (SEQ ID NO: 5) | 538 | 537.6 |
| Bz-Gly-Gly-Glu-Cys-Ala.amide (SEQ ID NO: 6) | 539 | 538.6 |
| Bz-Gly-(β)Dap-Gly-Cys-Ala.amide (SEQ ID NO: 7) | 496 | 495.6 |
| Bz-Gly-(β)Dap-Orn-Cys-Ala.amide | 553 | 552.7 |
| Bz-Gly-(β)Dap-(D)Orn-Cys-Ala.amide | 553 | 552.7 |
| Bz-Gly-(β)Dap-Met-Cys-Ala.amide (SEQ ID NO: 8) | 570 | 569.7 |
| Ac-Tyr-Gly-Gly-Gly-Cys-Ala.amide (SEQ ID NO: 9) | 568 | 567.6 |
| Ac-Tyr-Gly-Gly-Orn-Cys-Ala.amide (SEQ ID NO: 10) | 625 | 624.7 |
| Ac-Tyr-Gly-Gly-(D)Orn-Cys-Ala.amide | 625 | 624.7 |
| Ac-Tyr-Gly-Met-Gly-Cys-Ala.amide (SEQ ID NO: 11) | 642 | 641.8 |
| Ac-Tyr-Gly-Gln-Gly-Cys-Ala.amide (SEQ ID NO: 12) | 639 | 638.7 |
| Ac-Tyr-Gly-Glu-Gly-Cys-Ala.amide (SEQ ID NO: 13) | 640 | 639.7 |
| Ac-Tyr-Gly-(D)Orn-Gly-Cys-Ala.amide | 625 | 624.7 |
| Ac-Tyr-Gly-Gly-His-Cys-Ala.amide (SEQ ID NO: 14) | 648 | 647.7 |
| Ac-Tyr-Gly-(β)Dap-Gly-Cys-Ala.amide (SEQ ID NO: 15) | 597 | 597.3 |
| Ac-Tyr-Gly-(β)Dap($COCH_2CH_2NH_2$)-Gly-Cys-Ala.amide (SEQ ID NO: 16) | 668 | 668.3 |
| Ma-Gly-Gly-Tyr-Ala.amide (SEQ ID NO: 17) | 497 | 497.2 |
| Ma-(D)Orn-Gly-Tyr-Ala.amide | 554 | 554.3 |

EXAMPLE 2

Solid Phase Peptide Synthesis of Somatostatin Peptides

Cyclic somatostatin receptor-targeting peptides containing chelator moieties were also prepared by SPPS procedures. In general the peptides were made by coupling at pH 10 a choroacetylated, trityl-protected chelator tetra- or pentapeptide to a thiol function on a cyclic pharmacophore hexapeptide. The trityl protecting group was subsequently removed by treatment with TFA, and the final peptides were HPLC purified as described in Example 1.

A typical procedure for the coupling and final deprotection steps of the synthesis is outlined in FIG. 1.

The cyclic receptor-binding pharmacophore peptides were made using SPPS with Fmoc protection and with chlorotrityl resin as the solid-phase support. Linear protected hexapeptides were synthesized by SPPS using HBTU and piperidine, and then cleaved from the resin using hexafluoroisopropanol. For the sterically demanding couplings (for example between the resin-supported N-methylhomocysteine and Fmoc-phenylalanine), [O-(7-Azabenzotriazol-1-yl)-1,1,3,3-tetramethyuronium hexafluorophosphate (HATU) was utilized to preactivate the amino acid precursor. Homocysteine was N-methylated on the solid support by first forming the 2-nitrobenzenesulfonamide followed by deprotonation of the sulfonamide N—H with 1,3,4,6,7,8-Hexahydro-1-methyl-2H-pyrimido[1,2-a]pyrimidine (MTBD) and alkylation of the nitrogen with methyl iodide. Subsequent removal of the sulfonamide with mercaptoethanol and 1,8-Diazabicyclo[5.4.0]undec-7-ene (DBU) rendered the resin-supported peptide suitable for coupling to the next protected amino acid. The linear peptides were activated with HATU, cyclized, deprotected with TFA in water/triisopropylsilane/ethanedithiol, and HPLC purified. All cyclic pharmacophore peptides were >95% pure by HPLC and had the expected $MH^+$ peak by mass spectrometry.

The chelator peptides were also made by SPPS. For peptides in which the C-terminal functional group was either a carboxylic acid or an alcohol, chlorotrityl resin was used as the support. For peptides in which the C-terminal functional group was a carboxamide, Rink amide resin was used. Chloroacetic acid was added to the resin-supported peptides at the N-terminus. Peptides were cleaved from the resin using either hexafluoroisopropanol, or 95:5 (v/v) TFA/water. In the cases where hexafluoroisopropanol was used, the recovered peptides were fully protected. In the cases where TFA was used the tert-butyl-based protecting groups were removed. The trityl protecting group was selectively re-attached to the cysteine side-chain sulfhydryl group by concentrating in vacuo several times (redissolving the crude consecutively in chloroform) to remove the TFA. All chloroacetyl chelator peptides were >90% pure by HPLC and had the expected MH+ peak by FAB mass spectrometry.

Table 2 presents peptides prepared according to Example 2 along with MS results. All amino acids are in the L-form unless specified as D.

TABLE 2

| Compound | MS: M + H+ | $M_w$ calcd |
|---|---|---|
| cyclo-[Tyr-(D)Trp-Lys-Thr-Phe-(N-Me)Hcy]-CH$_2$CO.(β)Dap-Gly-Cys-Thr-Ser | 1249 | 1248.6 |
| cyclo-[Tyr-(D)Trp-Lys-Thr-Phe-(N-Me)Hcy]-CH$_2$CO.(β)Dap-(α)Dap-Cys-Thr-Ser | 1278 | 1276.9 |
| cyclo-[Tyr-(D)Trp-Lys-Thr-Phe-(N-Me)Hcy]-CH$_2$CO.(β)Dap-Dab-Cys-Thr-Ser | 1292 | 1291.0 |
| cyclo-[Tyr-(D)Trp-Lys-Thr-Phe-(N-Me)Hcy]-CH$_2$CO.(β)Dap-Orn-Cys-Thr-Ser | 1306 | 1305.8 |
| cyclo-[Tyr-(D)Trp-Lys-Thr-Phe-(N-Me)Hcy]-CH$_2$CO.(β)Dap-Lys-Cys-Thr-Ser | 1320 | 1319.8 |
| cyclo-[Tyr-(D)Trp-Lys-Thr-Phe-(N-Me)Hcy]-CH$_2$CO.(β)Dap-Met-Cys-Thr-Ser | 1323 | 1322.8 |
| cyclo-[(N-Me)Phe-Tyr-(D)Trp-Lys-Val-Hcy]-CH$_2$CO.(β)Dap-Gly-Cys-Lys-NH$_2$ | 1287 | 1286.7 |
| cyclo-[(N-Me)Phe-Tyr-(D)Trp-Lys-Val-Hcy]-CH$_2$CO.(β)Dap-(D)Orn-Cys-Lys-NH$_2$ | 1344 | 1343.8 |
| cyclo-[(N-Me)Phe-Tyr-(D)Trp-Lys-Val-Hcy]-CH$_2$CO.(β)Dap-Lys-Cys-Lys-NH$_2$ | 1358 | 1357.7 |

EXAMPLE 3

General Method for Radiolabeling with $^{99m}$Tc and $^{188}$Re

Lyophilized kit "placebo" vials were prepared containing 5 mg sodium glucoheptonate dihydrate, 100 μg edetate disodium dihydrate, and either 50 μg ($^{99m}$Tc placebo) or 1000 μg ($^{188}$Re placebo) stannous chloride dihydrate. The formulations were adjusted to pH 7.4 prior to lyophilization.

For the $^{99m}$Tc radiolabeling, a peptide as the TFA salt was dissolved in saline at 1 mg/mL and 100 μg (100 μL) was added to a $^{99m}$Tc placebo vial. The vial was reconstituted with 0.9 mL technetium $^{99m}$Tc sodium pertechnetate containing approximately 20 mCi and saline such that the final preparation volume was 1.1 mL. The vial was heated in a boiling water bath for 10 minutes and cooled at room temperature for 10 minutes.

For the $^{188}$Re radiolabeling, a peptide as the TFA salt was dissolved in saline at 1 mg/mL and 100 μg (100 μL) was added to a $^{188}$Re placebo vial. To the vial was added 100 μg stannous chloride dihydrate. The vial was reconstituted with 0.9 mL rhenium $^{188}$Re sodium perrhenate containing approximately 20 mCi and saline such that the final preparation volume was 1.5 mL. The vial was heated in a boiling water bath for 15 minutes and cooled at room temperature for 10 minutes. Finally 1 mL of an antioxidant stabilizer solution containing 10 mg gentisic acid sodium salt monohydrate and 20 mg ascorbic acid was added to the vial.

The radiochemical purity (RCP) of the $^{99m}$Tc or $^{188}$Re peptides was measured by gradient reversed phase HPLC using a Eurosphere-100 C18 HPLC column and 0.1% TFA mobile phases moderated with acetonitrile. Radioactive components were detected in the HPLC system using an in-line radiometric detector. Under the gradient conditions employed radiolabeled impurities (for example: $^{99m}$Tc glucoheptonate, $^{99m}$Tc edetate, and $^{99m}$Tc pertechnetate) eluted early (between 1 and 4 minutes), while the radiolabeled peptides eluted much later (between 8 and 20 minutes). In general, two isomeric radiometal complexes were observed, and the HPLC RCP was measured as the sum of the percent areas of the peaks corresponding to the two complexes. Radiochemical purity results for each of compounds are summarized in the examples that follow.

EXAMPLE 4

General Method for Cysteine Challenge Studies

To $^{99m}$Tc radiolabelled peptide preparations described in Example 3 was added 150 μg of cysteine (approximately a 7-fold molar excess over peptide), and the preparations were stored at room temperature and monitored by HPLC for up to 12 hours. The amount of $^{99m}$Tc cysteine formed over time was noted. The initial HPLC analysis was started within 5 minutes of adding cysteine. In all cysteine challenge studies, a chelator compound containing a stabilizing sidechain was screened vs. the corresponding control chelator compound containing no sidechain. The relative amount of $^{99m}$Tc cysteine formed over time correlates inversely with the stability of the chelator (ie. less $^{99m}$Tc cysteine indicates higher chelator stability).

EXAMPLE 5

Stability of $^{99m}$Tc Somatostatin Peptides

Figure 2:
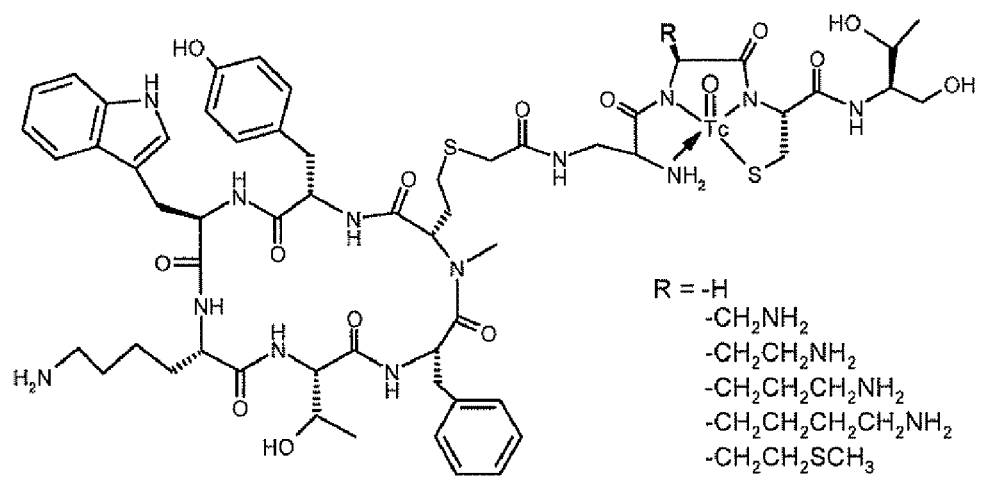
FIG. 2 shows peptides with varying sidechains in the chelator portions.

Somatostatin peptides were prepared with varying sidechains in the chelator portion of the compounds as described in FIG. 2. The sidechains varied in length from 0 to 5 atoms. These peptides have an amine-diamide-thiol chelator of the (β)Dap-N$^2$-Cys type (N$^2$=any amino acid). Each of the peptides were radiolabeled and monitored for HPLC stability out to 9 hours according the procedures described in Example 3. Results are tabulated in Table 3.

TABLE 3

| | HPLC RCP | | | |
|---|---|---|---|---|
| Sidechain | 0.5 hours | 3 hours | 6 hours | 9 hours |
| —H | 89.7 | 84.8 | 83.7 | 80.2 |
| —CH$_2$NH$_2$ | 88.5 | 86.6 | 84.1 | 82.6 |
| —CH$_2$CH$_2$NH$_2$ | 94.3 | 91.6 | 90.7 | 89.2 |
| —CH$_2$CH$_2$CH$_2$NH$_2$ | 97.0 | 95.2 | 94.9 | 94.9 |
| —CH$_2$CH$_2$CH$_2$CH$_2$NH$_2$ | 83.4 | 83.4 | 81.3 | 81.0 |
| —CH$_2$CH$_2$SCH$_3$ | 95.0 | 93.7 | 92.5 | 92.3 |

The results indicate that amine or thioether sidechains that are specifically 3-4 atoms in length improve the radiolableing yield and stability (relative to the peptide with no sidechain) of somatostatin peptides possessing the (β)Dap-N$^2$-Cys chelator. Amine sidechains of 2 atoms or 5 atoms in length did not show a stabilizing benefit.

EXAMPLE 6

Figure 3:
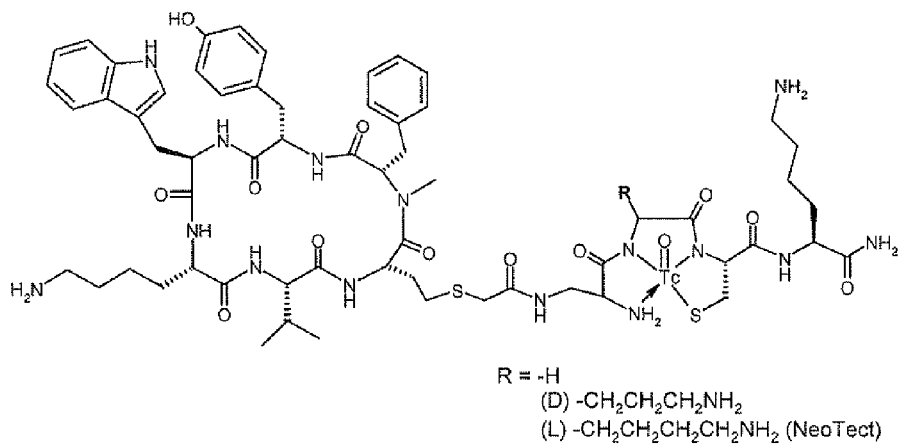
FIG. 3 shows analogs of NeoTect®.
Figure 4:
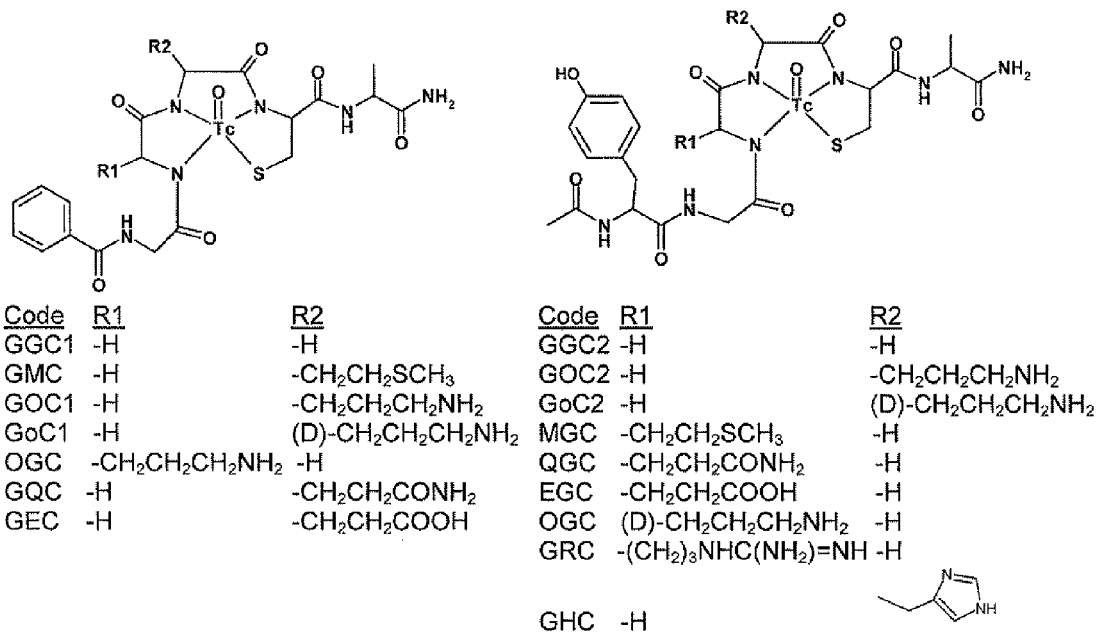
FIG. 4 shows sidechains substituted into a $N^1$—$N^2$-Cys chelator.

Stability of $^{99m}$Tc Somatostatin Peptides; Commercial Lung Cancer Diagnostic Agent Analogs Analogs to a commercial lung cancer imaging radiopharmaceutical (NeoTect®) were prepared to investigate the influence of the stabilizing sidechain (D)-$CH_2CH_2CH_2NH_2$ as described in FIG. 3. These peptides have an amine-diamide-thiol chelator of the (β)Dap-$N^2$-Cys type ($N^2$=any amino acid). The compound with $N^2$=Lys (sidechain=(L)-$CH_2CH_2$—$CH_2CH_2NH_2$) is the peptide in the commercial radiopharmaceutical product. Each of the peptides were radiolabeled and monitored for HPLC stability out to 18 hours according to the procedures described in Example 3. Results are tabulated in Table 4.

stituted into the $N^1$—$N^2$-Cys chelator in two positions $R_1$ and $R_2$ as depicted in FIG. 4. The compounds were screened in the cysteine challenge experiment described in Example 4. Several experiments were conducted where 1-2 chelators were compared directly to a control chelator containing no stabilizing sidechain (compound GoC1 was also analyzed alone in a further study). Results in Table 5 represent % Peptide complexed to $^{99m}$Tc (ie. 100%–the amount of $^{99m}$Tc cysteine) vs. time. These results are segregated according to each individual experiment.

TABLE 5

| | Sidechain | | % Peptide Complexed to $^{99m}$Tc | | | | | | |
|---|---|---|---|---|---|---|---|---|---|
| Code | Type | Position | Initial | 2 h | 4 h | 6 h | 8 h | 10 h | 12 h |
| GGC1 | none | n.a. | 98.8 | 83.6 | 74.0 | 74.3 | 68.3 | 65.0 | — |
| GOC1 | —$CH_2CH_2CH_2NH_2$ | R2 | 100 | 88.1 | 86.8 | 83.9 | 77.9 | 75.8 | — |
| GoC1 | (D)-$CH_2CH_2CH_2NH_2$ | R2 | 95.8 | 95.0 | 95.2 | 93.4 | 92.7 | 91.6 | — |
| GGC1 | none | n.a. | 96.9 | 85.2 | 71.7 | 72.0 | 61.7 | 60.0 | 49.7 |
| GQC | —$CH_2CH_2CONH_2$ | R2 | 97.8 | 93.2 | 88.7 | 82.4 | 80.1 | 78.7 | 73.5 |
| GEC | —$CH_2CH_2COOH$ | R2 | 100 | 88.9 | 84.5 | 80.3 | 75.7 | 74.1 | 69.0 |
| GGC1 | none | n.a. | 98.2 | 83.4 | 83.5 | 74.3 | 69.8 | 57.9 | 60.7 |
| OGC | —$CH_2CH_2CH_2NH_2$ | R1 | 100 | 91.9 | 83.3 | 78.5 | 69.5 | 67.0 | 59.6 |
| GMC | —$CH_2CH_2SCH_3$ | R2 | 96.9 | 92.6 | 88.6 | 83.7 | 82.7 | 78.6 | 77.2 |
| GoC1 | (D)-$CH_2CH_2CH_2NH_2$ | R2 | 96.7 | 95.7 | 95.5 | 95.0 | 93.7 | 92.0 | 94.7 |
| GGC2 | none | n.a. | 90.1 | 70.7 | 61.8 | 57.1 | 46.2 | 39.1 | 33.3 |
| GoC2 | (D)-$CH_2CH_2CH_2NH_2$ | R2 | 94.3 | 91.1 | 89.1 | 89.2 | 89.0 | 87.2 | 86.9 |
| oGC | (D)-$CH_2CH_2CH_2NH_2$ | R1 | 95.5 | 90.6 | 88.1 | 85.3 | 83.0 | 81.3 | 79.2 |
| GGC2 | none | n.a. | — | 80.7 | 72.0 | 65.7 | 61.0 | 59.0 | 57.2 |
| QGC | —$CH_2CH_2CONH_2$ | R1 | 92.9 | 88.7 | 88.8 | 86.6 | 85.6 | 83.8 | 84.2 |
| GHC | (imidazole sidechain) | R2 | 78.8 | 74.3 | 72.9 | 70.9 | 68.8 | 69.2 | 67.9 |
| GGC2 | none | n.a. | 92.0 | 79.3 | 70.5 | 65.6 | 57.8 | 55.1 | 44.5 |
| QGC | —$CH_2CH_2CONH_2$ | R1 | 96.3 | 88.3 | 86.1 | 84.0 | 82.0 | 77.6 | 75.9 |
| EGC | —$CH_2CH_2COOH$ | R1 | 91.4 | 84.1 | 78.1 | 73.3 | 67.4 | 60.1 | — |
| GGC2 | none | n.a. | 95.7 | 81.0 | 73.3 | 61.0 | 53.0 | 48.0 | 41.2 |
| MGC | —$CH_2CH_2SCH_3$ | R1 | 93.9 | 92.4 | 89.3 | 85.9 | 82.0 | 79.9 | 77.2 |
| GOC | —$CH_2CH_2CH_2NH_2$ | R2 | 98.2 | 93.8 | 90.0 | 86.1 | 80.0 | 78.1 | 88.6 |
| GGC2 | none | n.a. | 93.6 | 77.8 | 67.5 | 60.4 | 54.7 | 50.2 | 46.6 |
| GRC | —$(CH_2)_3NHC(NH_2)$=NH | R2 | 100 | 91.6 | 82.6 | 77.8 | 73.9 | 70.9 | 67.9 |

TABLE 4

| | HPLC RCP | | | | |
|---|---|---|---|---|---|
| C-Terminal Sequence | 0.5 hours | 3 hours | 6 hours | 9 hours | 18 hrs. |
| -(β)Dap-Lys-Cys-Lys-$NH_2$ | 93.9 | 91.0 | 85.2 | 81.8 | 75.7 |
| -(β)Dap-Gly-Cys-Lys-$NH_2$ | 92.3 | 84.9 | 85.6 | 81.3 | 76.0 |
| -(β)Dap-(D)Orn-Cys-Lys-$NH_2$ | 96.8 | 94.1 | 91.3 | 89.8 | 81.9 |

The results indicate that the stabilizing amine sidechain (D)-$CH_2CH_2CH_2NH_2$ is capable of improving the radiolabeling performance of the peptide of a commercial radiopharmaceutical product.

EXAMPLE 7

Cysteine Challenge Stability of $^{99m}$Tc Chelator Peptides; $N^1$—$N^2$-Cys Triamide Thiol Chelators Several model chelator peptides were prepared with an $N^1$—$N^2$-Cys ($N^1$, $N^2$=independently any amino acid) amino acid sequence capable of complexing technetium as a triamide thiol chelator. Various stabilizing sidechains were sub- The results indicate that all of the sidechains investigated stabilized the $^{99m}$Tc complexes to the cysteine challenge relative to the no-sidechain control chelators. Several types of donor atoms are effective on the sidechains (amine, amide, or imidazole nitrogens, thioether sulfurs, or carboxylic acid oxygens), and the sidechains can be located in different positions along the ligand chelate backbone.

EXAMPLE 8

Figure 5:
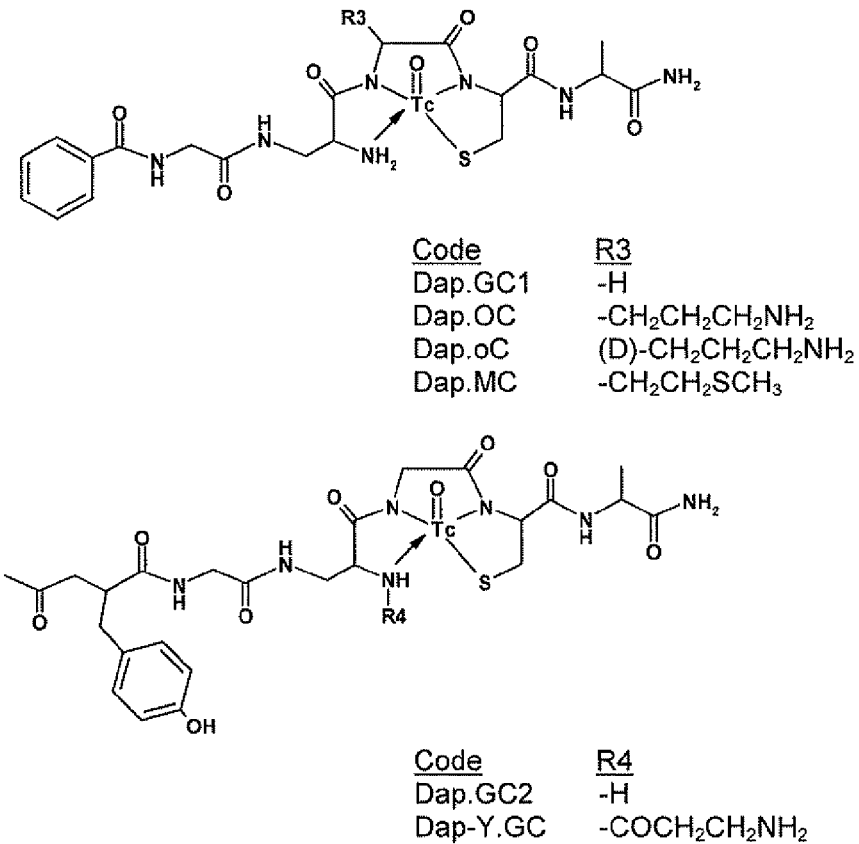
FIG. 5 shows sidechains substituted into a (β)Dap-$N^2$-Cys chelator.

Cysteine Challenge Stability of $^{99m}$Tc Chelator Peptides; (β)Dap-$N^2$-Cys Amine Diamide Thiol Chelators Several model chelator peptides were prepared with an (β)Dap-$N^2$-Cys ($N^2$=any amino acid) amino acid sequence capable of complexing technetium as an amine diamide thiol chelator. This chelator is the chelator in the somatostatin peptides that were evaluated in Examples 5 and 6. Various stabilizing sidechains were substituted into the (β)Dap-$N^2$-Cys chelator in two positions $R_3$ and $R_4$ as depicted in FIG. 5. The compounds were screened in the cysteine challenge experiment described in Example 4. Several experiments were conducted where 1-2 chelators were compared directly to a control chelator containing no stabilizing sidechain. Results in Table 6 are the same as described in Example 7.

TABLE 6

| | Sidechain | | % Peptide Complexed to $^{99m}$Tc | | | | | | |
|---|---|---|---|---|---|---|---|---|---|
| Code | Type | Position | Initial | 2 h | 4 h | 6 h | 8 h | 10 h | 12 h |
| Dap.GC1 | none | n.a. | — | 78.1 | 62.7 | 57.8 | 51.9 | — | 43.3 |
| Dap.OC | —CH$_2$CH$_2$CH$_2$NH$_2$ | R3 | 98.4 | 93.8 | 90.5 | 86.4 | 91.3 | 75.2 | 80.0 |
| Dap.MC | —CH$_2$CH$_2$SCH$_3$ | R3 | 97.4 | 95.4 | 89.8 | 92.6 | 91.6 | 88.4 | 89.7 |
| Dap.GC | none | n.a. | 81.7 | 78.9 | 42.6 | 51.6 | 46.3 | 46.2 | 37.6 |
| Dap.OC | —CH$_2$CH$_2$CH$_2$NH$_2$ | R3 | 96.0 | 94.5 | 93.2 | 91.7 | 90.3 | 89.4 | 84.8 |
| Dap.oC | —CH$_2$CH$_2$SCH$_3$ | R3 | 100 | 93.5 | 87.7 | 89.9 | 77.7 | 78.0 | 85.4 |
| Dap.GC2 | none | n.a. | 83.4 | 67.7 | 55.1 | 49.6 | 44.7 | 38.0 | 38.7 |
| Dap-Y.GC | —COCH$_2$CH$_2$NH$_2$ | R4 | 93.7 | 84.6 | 84.1 | 82.9 | 80.7 | 80.0 | 77.2 |

The results indicate that the amine diamide thiol chelators can be stabilized by the stabilizing sidechains. These model chelator cysteine challenge results confirm the results reported in Examples 5 and 6 for the somatostatin peptides. In addition, the results for the Dap-Y.GC compound indicate that the stabilizing sidechain can be appended to the donor atoms of chelate ligand backbone.

EXAMPLE 9

Figure 6:
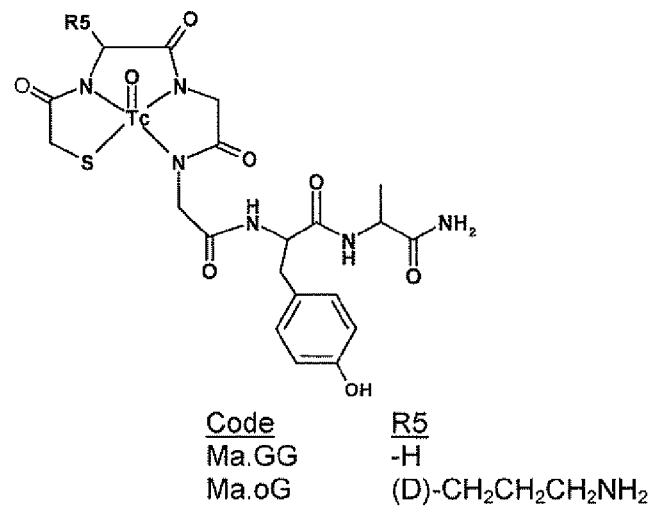
FIG. 6 shows a stabilizing sidechain substituted into a ma-$N^1$—$N^2$-chelator.

Cysteine Challenge Stability of $^{99m}$Tc Chelator Peptides; Ma-N$^1$—N$^2$ Tramide Thiol Chelators Two model chelator peptides were prepared with a ma-N$^1$—N$^2$ (Ma=mercaptoacetyl; N$^1$, N$^2$=independently any amino acid) amino acid sequence capable of complexing technetium as a triamide thiol chelator. This chelator has the thiol donor group at the N-terminus of the peptide. A stabilizing sidechain was substituted into the ma-N$^1$—N$^2$ chelator in position R$_5$ as depicted in FIG. 6. The compounds were radiolabeled according to Example 3 with the exception that additional NaOH was added to bring the pH of the preparation up to pH 8.5. The radiolabeled compounds were then screened in the cysteine challenge experiment described in Example 4. Results in Table 7 are the same as described in Example 7.

TABLE 7

| | Sidechain | | % Peptide Complexed to $^{99m}$Tc | | | | | | |
|---|---|---|---|---|---|---|---|---|---|
| Code | Type | Position | Initial | 2 h | 4 h | 6 h | 8 h | 10 h | 12 h |
| Ma.GG | none | n.a. | 100 | 91.3 | 75.7 | 61.2 | 48.7 | 42.2 | 32.7 |
| Ma.oC | (D)-CH$_2$CH$_2$CH$_2$NH$_2$ | R5 | 100 | 87.4 | 87.2 | 84.9 | 85.9 | 84.1 | 82.7 |

The results indicate that the stabilizing sidechains can also stabilize the Ma-N$^1$—N$^2$ type of chelators with the thiol donor on the N-terminal side of the peptide.

EXAMPLE 10

Cysteine Challenge Stability of $^{188}$Re Chelator Peptides; N$^1$—N$^2$-Cys Triamide Thiol Chelators Some of the N$^1$—N$^2$-Cys (N$^1$, N$^2$=independently any amino acid) model chelator peptides described in Example 7 were radiolabeled with $^{188}$Re and screened in the cysteine challenge experiment described in Example 4. Two chelators (See FIG. 4) were compared directly to the control chelator containing no stabilizing sidechain. In these studies, the products were monitored for 6 hours. Results in Table 8 represent % Peptide complexed to $^{188}$Re (ie. 100%–the amount of $^{188}$Re cysteine) vs. time. These results are segregated according to each individual experiment.

TABLE 8

| | Sidechain | | % Peptide Complexed to $^{99m}$Tc | | | | |
|---|---|---|---|---|---|---|---|
| Code | Type | Position | Initial | 1.5 h | 3 h | 4.5 h | 6 h |
| GGC1 | none | n.a. | 100 | 80.1 | 61.4 | 50.2 | 47.7 |
| GEC | —CH$_2$CH$_2$COOH | R2 | 98.0 | 94.0 | 90.5 | 89.7 | 90.2 |
| GGC1 | none | n.a. | 100 | 80.1 | 61.4 | 50.2 | 47.7 |
| GoC1 | (D)-CH$_2$CH$_2$CH$_2$NH$_2$ | R2 | 100 | 94.9 | 91.4 | 91.3 | 88.5 |

The results indicate that the stabilizing sidechains can also stabilize $^{188}$Re complexes.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 05005295.0, filed Mar. 10, 2005 and U.S. Provisional Application Ser. No. 60/659,875, filed Mar. 10, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A conjugate PT comprising
   (a) a peptide P and
   (b) a targeting moiety T;

wherein the peptide P contains from 4 to 20 amino acid residues, and including a complexing amino acid sequence comprising
   (i) a tridentate or tetradentate planar chelator containing a ligand backbone defined by a perimeter containing
      a single sulfur donor atom,
      two or three non-sulfur donor atoms, and
      intervening atoms between the donor atoms; and
   (ii) a stabilizing sidechain comprising a further donor atom, the further donor atom being covalently linked to the ligand backbone of the planar chelator through two or three intervening atoms, provided that
   said further donor atom is neither the nitrogen nor the oxygen atom of a peptide bond, and if said further donor atom is part of a heterocyclic ring, no more than one of the intervening atoms can be part of that ring; and (iii) a radioactive metal complexed to the donor atoms of the planar chelator, wherein the planar chelator comprises a single thiol amino acid or single thiol moiety containing the single sulfur donor atom of the ligand backbone, the single thiol amino acid or single thiol moiety having a structure of formula (I)

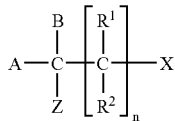
(I)

wherein
A is —$CO_2H$, —$CONH_2$, —$CO_2$-(pep), —CONH-(pep), or $R^4$;
B is —SH, —$NHR^3$, —$N(R^3)$-(pep), or $R^4$;
X is —SH, —$NHR^3$, —$N(R^3)$-(pep), or $R^4$;
Z is —H or —$CH_3$;
n is 0, 1, or 2;
$R^1$, $R^2$, $R^3$, and $R^4$ are independently —H or —$C_1$-$C_6$-alkyl;
(pep) represents the remainder of the peptide P and its complexing amino acid sequence, respectively;
provided that either
(i) B is —SH; X is —$NHR^3$ or —$N(R^3)$-(pep); and n is 1 or 2; or
(ii) A is $R^4$; B is —SH; and X is —$N(R^3)$-(pep); or
(iii) A is $R^4$; B is —$N(R^3)$-(pep); and X is —SH; or
(iv) A is —$CO_2$-(pep) or —CONH-(pep); B is —SH; X is —$CH_3$; Z is —$CH_3$; and n is 0;
and provided that if the targeting moiety T is a cyclic somatostatin derivative or cyclic somatostatin receptor binding peptide, then the stabilizing sidechain is not —$CH_2CH_2CH_2NH_2$, —$CH_2CH_2NH_2$, —$CH_2$-(4-imidazolyl), or —$CH_2CH_2CH_2NHC(NH)NH_2$; and if the targeting moiety T is folate or folic acid or an analog thereof, then the stabilizing side chain is not —$CH_2COOH$.

2. The conjugate according to claim 1, wherein the peptide P contains at least 6 amino acid residues.

3. The conjugate according to claim 1, wherein the further donor atom of the stabilizing sidechain is not a tertiary amine nitrogen donor atom.

4. The conjugate according to claim 1, wherein
(i) A is —CONH-(pep); B is —SH; X is —$N(R^3)$-(pep); Z is —H; n is 1; and $R^1$, $R^2$ and $R^3$ are —H;
or
(ii) A is —$CH_3$; B is —SH; X is —$N(R^3)$-(pep); Z is —H; n is 1; and $R^1$, $R^2$ and $R^3$ are —H; or
(iii) A is —$CH_3$; B is —$N(R^3)$-(pep); X is —SH; Z is —H; n is 1; and $R^1$, $R^2$ and $R^3$ are —H; or
iv) A is —CONH-(pep); B is —SH; X is —$CH_3$; Z is —$CH_3$; and n is 0.

5. The conjugate according to claim 1, wherein the non-sulfur donor atoms are nitrogen donor atoms.

6. The conjugate according to claim 1, wherein the complexing amino acid sequence comprises a structure of formula (II)

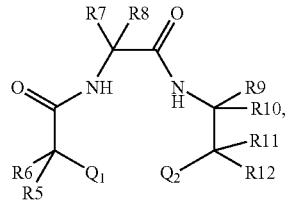
(II)

wherein
$Q_1$ is —SH, and
$Q_2$ is —N-(pep), —N-(sidechain) or —$NR_2$;
or
$Q_2$ is —SH, and
$Q_1$ is —N-(pep), —N-(sidechain) or —$NR_2$;
R are each independently —H or —$C_1$-$C_6$-alkyl;
$R^5$ and $R^6$ are independently E, -(pep) or -(sidechain);
$R^7$, $R^8$, $R^9$ and $R^{10}$ are independently E, -(pep) or -(sidechain); and
$R^{11}$ and $R^{12}$ are independently E or -(pep), or
$R^{11}$ and $R^{12}$ together with the carbon atom to which they are attached form a carbonyl group;
E is independently —H, —$C_1$-$C_4$-alkyl, —$CH_2OH$, —$CH_2NH_2$, —$CH(OH)CH_3$, —$CH_2C_6H_5$, —$CH_2CH_2C_6H_5$, —$CH_2$-(p-$C_6H_4$—OH), —$CH_2$-(p-$C_6H_4$—$NH_2$), —$CH_2$-(p-$C_6H_4$—F), —$CH_2$-(p-$C_6H_4$—Cl), —$CH_2$-(p-$C_6H_4$—I), —$CH_2$-(p-$C_6H_4$—Br), —$CH_2CH_2$—$CH_2CH_2NH_2$, —$CH_2$-(3-indolyl), —$CH_2CH_2CH_2COOH$, —$CH_2CH_2CH_2$—$CH_2CH_2CH_2COOH$, —$CH_2C_6H_{11}$, —$CH_2SCH_2CH(COOH)NH_2$, —$C_6H_5$, —$CH_2$-(1-naphthyl), —$CH_2$-(2-naphthyl) —$C_6H_{11}$, —$CH_2C\equiv CH$, —$C(CH_3)_3$, —$CH_2$-(p-$C_6H_4$—$COC_6H_5$), or —$CH_2$-(p-$C_6H_4$—$C_6H_5$);
(pep) represents the remainder of the peptide P and its complexing amino acid sequence; and
(sidechain) represents the stabilizing sidechain comprising a further donor atom; provided that the structure of formula (II) comprises at least one moiety (pep) and at least one moiety (sidechain).

7. The conjugate according to claim 1, wherein the complexing amino acid sequence comprises a sequence (pep)-$N^1$—$N^2$—C-(pep); (pep)-$N^1$—$N^2$—C; $N^1$—$N^2$—C-(pep); (pep)-$N^1$—$N^2$-Aet, (pep)-$N^1$—$N^2$-Aet(sidechain1), (pep)-$N^1$—$N^2$-Aet(sidechain2), (pep)-$N^1$—$N^2$-Apt, (pep)-$N^1$—$N^2$-Apt(sidechain), (pep)-$N^1$—$N^2$-Mpa, (pep)-$N^1$—$N^2$-Mpa(sidechain1), (pep)-$N^1$—$N^2$-Mpa(sidechain2); (pep)-$N^1$—$N^2$-Mma, (pep)-$N^1$—$N^2$-Mma(sidechain), (pep)-C—$N^2$—$N^3$; C—$N^2$—$N^3$-(pep), Ma-$N^2$—$N^3$-(pep), Ma(sidechain)-$N^2$—$N^3$-(pep), Mp-$N^2$—$N^3$-(pep), Mp(sidechain) -$N^2$—$N^3$-(pep), or Mmp-$N^2$—$N^3$-(pep);
wherein
(pep) is the remainder of the peptide P;
C is (R) iso-Cys, (S) iso-Cys, or sidechain-substituted Cys or iso-Cys of the following formulas

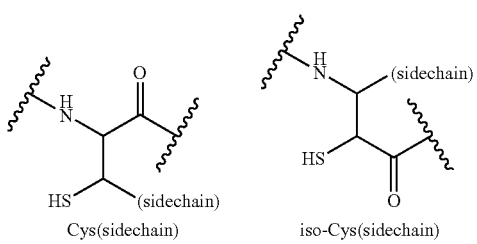

Mp means 2-mercaptopropionyl;
Mpa means 2-mercaptopropylamino,
Apt means 2-amino-propanethiol;
Mmp means 2-mercapto-2-methyl-propionyl;
Aet means 2-amino-ethanethiol;
Mma means 2-mercapto-2-methylpropylamino;
Aet(sidechain1), Aet(sidechain2), Apt(sidechain), Mpa(sidechain1), Mpa(sidechain2), and Mma(sidechain) are of the following formulas

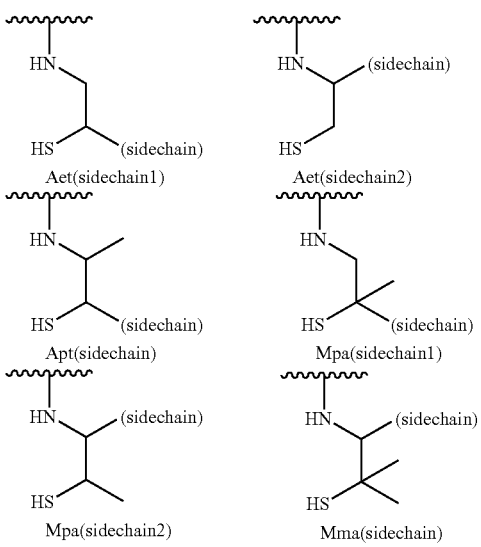

Ma(sidechain) and Mp(sidechain) are of the following formulas

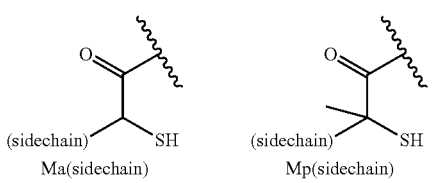

—$N^1$—, —$N^2$— and —$N^3$— are independently
(i) an α- or β-(homo) amino acid residue with 0, 1 or 2 hydrocarbon sidechains that are saturated or unsaturated, and linear, branched, homocyclic, or heterocyclic, and optionally comprising one or more hydroxyl, carbonyl, ether, thioether, carboxyl, amide, amine, nitro, nitroso, azido, aldehyde, ketone, aryl, heteroaryl, halide, ester, cyano, or glycosyl functional groups; or
(ii) a heterocyclic amine-containing amino acid residue that is a saturated or unsaturated hydrocarbon, and optionally comprising one or more hydroxyl, carbonyl, ether, thioether, carboxyl, amide, amine, nitro, nitroso, azido, aldehyde, ketone, aryl, heteroaryl, halide, ester, cyano or, glycosyl functional groups; or
(iii) an amino acid residue of formula (III a), (III b), or (III c)

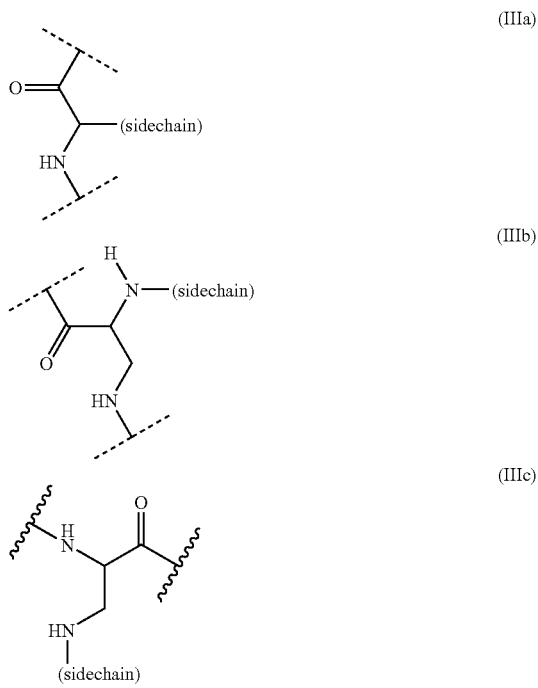

wherein
when —$N^1$—, —$N^2$— or —$N^3$— are α- or β-(homo) amino acids and when these amino acids contain a chiral carbon atom, they are optionally D- or L-; and
when —$N^1$— or —$N^2$— are α- or β-(homo) amino acids, then they are optionally in the N—$C_1$-$C_6$-alkyl form; or
—$N^1$— is a ω-amine-linked D- or L-diamino acid of the structure HOOC—CH(NH$_2$)—(CH$_2$)$_p$—NH$_2$, or
—$N^3$— is D-Dap, L-Dap, D-(β)Dap, L-(β)Dap or a ω-amine-linked amino acid of the structure HOOC—(CH$_2$)$_p$—CH(NH$_2$)CH$_2$—NH$_2$, wherein p is an integer of 1 to 10, wherein the remainder of the peptide toward the N-terminus is linked at either amine group, and wherein (β)Dap means β-diaminopropionic acid.

8. The conjugate according to claim 7, wherein
—$N^1$— is Gly; and
—$N^2$— is an amino acid residue Met, Orn, (D)Orn, Gln, Glu, Arg, or His;

or
—$N^1$— is an amino acid residue Met, Orn, (D)Orn, Gln, Glu, Arg, His or (β)Dap(COCH$_2$CH$_2$NH$_2$); and
—$N^2$— is Gly;

or
—$N^2$— is Gly; and
—$N^3$— is an amino acid residue Met, Orn, (D)Orn, Gln, Glu, Arg, or His;

or
—$N^2$— is an amino acid residue Met, Orn, (D)Orn, Gln, Glu, Arg, or His; and
—$N^3$— is Gly;

wherein (β)Dap(COCH₂CH₂NH₂) represents an amino acid residue of formula (III b), wherein —(sidechain) is —COCH₂CH₂NH₂.

9. The conjugate according to claim 1, wherein the further donor atom of the stabilizing sidechain is N, P, O or S.

10. The conjugate according to claim 1, wherein the stabilizing sidechain has a structure of formula (IV a), (IV b), (IV c) or (IV d)

$$-(Y^1)_n-D \qquad \text{(IV a)}$$

$$-(Y^1)_{n-1}-Y^2-D \qquad \text{(IV b)}$$

$$-Y^3-(Y^1)_{n-1}-D \qquad \text{(IV c)}$$

$$-Y^3-Y^2-(Y^1)_{n-2}-D \qquad \text{(IV d)}$$

wherein
n is 2 or 3;
$Y^1$ is —C($R^{15}R^{16}$)—, —$NR^{17}$—, —O—, or —S—;
$Y^2$ is —C($R^{18}R^{19}$)—, —$NR^{20}$—, —O—, or —S—;
$Y^3$ is —C($R^{21}R^{22}$)—, —$NR^{23}$—, —O—, or —S—;
D is —$NR^{24}R^{25}$, —$OR^{26}$, —$SR^{26}$, or —$PR^{27}R^{28}$;
$R^{15}$ and $R^{16}$ are independently —H, -OH, —CO₂H, —C₁-C₆-alkyl, —C₁-C₄-alkyl-OH, or —CO—C₁-C₆-alkyl,
or
$R^{15}$ and $R^{16}$ together with the carbon atom to which they are attached form a carbonyl group or an imino group;
$R^{17}$ is —H, —OH, —C₁-C₆-alkyl, —C₁-C₄-alkyl-OH or —CO—C₁-C₆-alkyl;
$R^{18}$ and $R^{19}$ are independently —H, —OH, —CO₂H, —C₁-C₆-alkyl, —C₁-C₄-alkyl-OH, or —CO—C₁-C₆-alkyl,
or
$R^{18}$ and $R^{19}$ together with the carbon atom to which they are attached form a carbonyl group;
$R^{20}$ is —H, —OH, —C₁-C₆-alkyl, —C₁-C₄-alkyl-OH or —CO—C₁-C₆-alkyl;
$R^{21}$ and $R^{22}$ are independently —H, —OH, —CO₂H, —C₁-C₆-alkyl, —C₁-C₄-alkyl-OH, or —CO—C₁-C₆-alkyl,
or
$R^{21}$ and $R^{22}$ together with the carbon atom to which they are attached form a carbonyl group;
$R^{23}$ is —H, —OH, —C₁C₆-alkyl, —C₁-C₄-alkyl-OH, or —CO—C₁-C₆-alkyl;
$R^{24}$ and $R^{25}$ are independently —H, —OH, —C₁-C₆-alkyl, —C₁-C₄-alkyl-OH, —CO—C₁-C₆-alkyl, —C(NH₂)=NH₂, or —CONH₂;
$R^{26}$ is —H, —C₁-C₆-alkyl, —C₁-C₄-alkyl-OH, or —CO—C₁-C₆-alkyl,
or
$R^{15}$ or $R^{17}$ together with $R^{18}$, $R^{20}$, $R^{21}$, or $R^{23}$ form a 4 to 6 membered saturated or unsaturated ring;
or
$R^{18}$ or $R^{20}$ together with $R^{24}$ or $R^{26}$ form a 4 to 6 membered saturated or unsaturated ring containing 1 to 4 N, O and/or S atoms; and
$R^{27}$ and $R^{28}$ are independently —H, —OH, —C₁-C₆-alkyl, —C₁-C₆-alkyl-CO₂H, —C₁-C₄-alkyl-OH or —O—C₁-C₆-alkyl.

11. The conjugate according to claim 10, wherein the stabilizing sidechain has a structure of formula (IV a), (IV b) or (IV c),
wherein
n is 2 or 3;
$Y^1$ is —C($R^{15}R^{16}$)—;
$Y^2$ is —C($R^{18}R^{19}$)—;
$Y^3$ is —C($R^{21}R^{22}$)—;
D is —$NR^{24}R^{25}$, —$OR^{26}$, or —$SR^{26}$;
$R^{15}$ and $R^{16}$ are —H;
$R^{18}$ and $R^{19}$ are —H;
or
$R^{18}$ and $R^{19}$ together with the carbon atom to which they are attached form a carbonyl group;
$R^{21}$ and $R^{22}$ together with the carbon atom to which they are attached form a carbonyl group;
$R^{24}$ and $R^{25}$ are —H;
$R^{26}$ is —H or —C₁-C₆-alkyl;
or
$R^{18}$ together with $R^{24}$ forms a 4 to 6 membered saturated or unsaturated ring containing 2 or 3 N, O and/or S atoms.

12. The conjugate according to claim 10, wherein the stabilizing sidechain is —CH₂CH₂NH₂, —CH₂CH₂CH₂NH₂, —CH₂CH₂CH₂NHCONH₂, —CH₂CH₂CH₂NHC(NH)NH₂, —CH₂CH(CO₂H)₂, —CH₂CH₂CONH₂, —CH₂CH₂COOH, —COCH₂CH₂NH₂, —CH₂CH₂—SCH₃, or —CH₂-(4-imidazolyl).

13. The conjugate according to claim 1 wherein the radioactive metal is $^{46}$Sc, $^{47}$Sc, $^{60}$Cu, $^{62}$Cu, $^{64}$Cu, $^{67}$Cu, $^{66}$Ga, $^{67}$Ga, $^{68}$Ga, $^{86}$Y, $^{90}$Y, $^{94m}$Tc, $^{99}$Tc, $^{99m}$Tc, $^{105}$Rh, $^{103}$Pd, $^{111}$In, $^{142}$Pr, $^{149}$Pm, $^{153}$Sm, $^{159}$Gd, $^{166}$Ho, $^{177}$Lu, $^{186}$Re, $^{188}$Re, $^{199}$Pt, $^{213}$Bi, $^{225}$Ac, $^{52}$Fe, $^{62}$Zn, $^{89}$Zr, $^{103}$Ru, $^{161}$Tb or $^{117m}$Sn.

14. The conjugate according to claim 13, wherein the radioactive metal is $^{60}$Cu, $^{62}$Cu, $^{64}$Cu, $^{67}$Cu, $^{94m}$Tc, $^{99}$Tc, $^{99m}$Tc, $^{103}$Pd, $^{186}$Re, $^{188}$Re or $^{199}$Pt.

15. The conjugate according to claim 1, which does not contain amino acid residues derived from a β-homo amino acid, cyclic amino acid or N-methyl amino acid.

16. A conjugate PT comprising
(a) a peptide P and
(b) a targeting moiety T;
wherein the peptide P contains from 4 to 20 amino acids, and including a complexing amino acid sequence comprising
(i) a tridentate or tetradentate planar chelator containing a ligand backbone defined by a perimeter containing
a single sulfur donor atom,
two or three non-sulfur donor atoms, and
intervening atoms between the donor atoms; and
(ii) a stabilizing sidechain comprising a further donor atom, the further donor atom being covalently linked to the ligand backbone of the planar chelator through two or three intervening atoms, provided that
said further donor atom is neither the nitrogen nor the oxygen atom of a peptide bond and
if said further donor atom is part of a heterocyclic ring, no more than one of the intervening atoms can be part of that ring and
the stabilizing side chain is not linked at the standard alpha positions of amino acids in P; and
(ii) a radioactive metal complexed to the donor atoms of the planar chelator,
wherein the planar chelator comprises a single thiol amino acid or single thiol moiety containing the single sulfur donor atom of the ligand backbone, the single thiol amino acid or single thiol moiety having a structure of formula (I)

$$\begin{array}{c} \text{B} \quad \begin{bmatrix} R^1 \\ | \end{bmatrix} \\ A-C-\begin{bmatrix} C \\ | \end{bmatrix}-X \\ | \quad \begin{bmatrix} | \\ R^2 \end{bmatrix}_n \\ Z \end{array}$$ (I)

wherein
A is —$CO_2H$, —$CONH_2$, —$CO_2$-(pep), —CONH-(pep), or $R^4$;
B is —SH, —$NHR^3$, —$N(R^3)$-(pep), or $R^4$;
X is —SH, —$NHR^3$, —$N(R^3)$-(pep), or $R^4$;
Z is —H or —$CH_3$;
n is 0, 1, or 2;
$R^1$, $R^2$, $R^3$, and $R^4$ are independently —H or —$C_1$-$C_6$-alkyl;
(pep) represents the remainder of the peptide P and its complexing amino acid sequence, respectively;
provided that either
(i) B is —SH; X is —$NHR^3$ or —$N(R^3)$-(pep); and n is 1 or 2; or
(ii) A is $R^4$; B is —SH; and X is —$N(R^3)$-(pep); or
(iii) A is $R^4$; B is —$N(R^3)$-(pep); and X is —SH; or
(iv) A is —$CO_2$-(pep) or —CONH-(pep); B is —SH; X is —$CH_3$; Z is —$CH_3$; and n is 0.

17. The conjugate according to claim 16, wherein the complexing amino acid sequence comprises a structure of formula (V)

$$\begin{array}{c} R^7 \ R^8 \quad O \\ | \ | \quad \| \\ O \quad NH \quad N \quad R^9 \\ \| \quad | \quad | \quad R^{10}, \\ \quad \quad H \quad R^{11} \\ R^6 \ Q_1 \quad Q_2 \quad R^{12} \\ R^5 \end{array}$$ (V)

wherein
$Q_1$ is —SH, and
$Q_2$ is —N-(pep), —N-(sidechain) or —$NR_2$; or
$Q_2$ is —SH, and
$Q_1$ is —N-(pep), —N-(sidechain) or —$NR_2$;
R are each independently —H or —$C_1$-$C_6$-alkyl;
$R^5$ and $R^6$ are independently E, -(pep) or -(sidechain), except when $Q_2$ is —SH, then $R^5$ and $R^6$ are not -(sidechain);
$R^7$ and $R^8$ are independently E or -(pep),
$R^9$ and $R^{10}$ are independently E, -(pep) or -(sidechain), except when $R^{11}$ and $R^{12}$ together with the carbon atom to which they are attached form a carbonyl group, then $R^9$ and $R^{10}$ are not -(sidechain);
$R^{11}$ and $R^{12}$ are independently E or -(pep),
or
$R^{11}$ and $R^{12}$ together with the carbon atom to which they are attached form a carbonyl group;
E is independently —H, —$C_1$-$C_4$-alkyl, —$CH_2OH$, —$CH_2NH_2$, —CH(OH)$CH_3$, —$CH_2C_6H_5$, —$CH_2CH_2C_6H_5$, —$CH_2$-(p-$C_6H_4$—OH), —$CH_2$-(p-$C_6H_4$—$NH_2$), —$CH_2$-(p-$C_6H_4$—F), —$CH_2$-(p-$C_6H_4$—Cl), —$CH_2$-(p-$C_6H_4$—I), —$CH_2$-(p-$C_6H_4$—Br), —$CH_2CH_2$—$CH_2CH_2NH_2$, —$CH_2$-(3-indolyl), —$CH_2CH_2CH_2COOH$, —$CH_2CH_2$—$CH_2CH_2CH_2COOH$, —$CH_2C_6H_{11}$, —$CH_2SCH_2CH$(COOH)$NH_2$, —$C_6H_5$, —$CH_2$-(1-naphthyl), —$CH_2$-(2-naphthyl) —$C_6H_{11}$, —$CH_2C\equiv CH$, —$C(CH_3)_3$, —$CH_2$- (p-$C_6H_4$—$COC_6H_5$), or —$CH_2$-(p-$C_6H_4$—$C_6H_5$);
(pep) represents the remainder of the peptide P and its complexing amino acid sequence; and
(sidechain) represents the stabilizing sidechain comprising a further donor atom;
provided that the structure of formula (V) comprises at least one moiety (pep) and at least one moiety (sidechain).

18. A conjugate according to claim 16, wherein the complexing amino acid sequence comprises (pep)-$N^1$—$N^2$-C-(pep); (pep)-$N^1$—$N^2$—C; $N^1$—$N^2$—C-(pep); (pep)-$N^1$—$N^2$-Aet, (pep)-$N^1$—$N^2$-Aet(sidechain 1), (pep)-$N^1$—$N^2$-Aet (sidechain2), (pep)-$N^1$—$N^2$-Apt, (pep)-$N^1$—$N^2$-Apt (sidechain), (pep)-$N^1$—$N^2$-Mpa, (pep)-$N^1$—$N^2$-Mpa (sidechain1), (pep)-$N^1$—$N^2$ -Mpa (sidechain2); (pep)-$N^1$—$N^2$-Mma, (pep)-$N^1$—$N^2$-Mma(sidechain), (pep)-C —$N^2$—$N^3$; C —$N^2$—$N^3$-(pep), Ma-$N^2$—$N^3$-(pep), Ma(sidechain)-$N^2$—$N^3$-(pep), Mp-$N^2$—$N^3$-(pep), Mp(sidechain)-$N^2$—$N^3$-(pep), or Mmp-$N^2$—$N^3$-(pep);
wherein
(pep) is the remainder of the peptide P;
C is (R) iso-Cys, (S) iso-Cys, or sidechain-substituted Cys or iso-Cys of the following formulas Cys(sidechain)      iso-Cys(sidechain)

Mp means 2-mercaptopropionyl;
Ma means 2-mercaptoacetyl;
Mpa means 2-mercaptopropylamino,
Apt means 2-amino-propanethiol;
Mmp means 2-mercapto-2-methyl-propionyl;
Aet means 2-amino-ethanethiol;
Mma means 2-mercapto-2-methylpropylamino;
Aet(sidechain1), Aet(sidechain2), Apt(sidechain), Mpa (sidechain1), Mpa(sidechain2), and
Mma(sidechain) are of the following formulas Aet(sidechain1)      Aet(sidechain2)

Apt(sidechain)      Mpa(sidechain1)

-continued

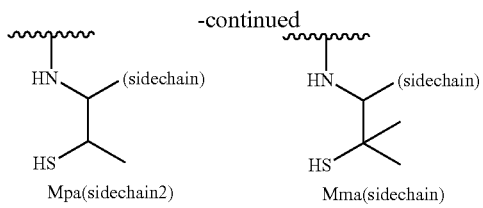

Ma(sidechain) and Mp(sidechain) are of the following formulas

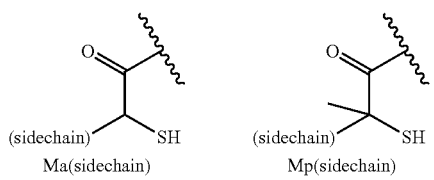

—N$^1$—, —N$^2$— and —N$^3$— are independently
(i) an α- or β-(homo) amino acid residue with 0, 1 or 2 hydrocarbon sidechains that are saturated or unsaturated, and linear, branched, homocyclic, or heterocyclic, and optionally comprising one or more hydroxyl, carbonyl, ether, thioether, carboxyl, amide, amine, nitro, nitroso, azido, aldehyde, ketone, aryl, heteroaryl, halide, ester, cyano, or glycosyl functional groups; or
(ii) a heterocyclic amine-containing amino acid residue that is a saturated or unsaturated hydrocarbon, and optionally comprising one or more hydroxyl, carbonyl, ether, thioether, carboxyl, amide, amine, nitro, nitroso, azido, aldehyde, ketone, aryl, heteroaryl, halide, ester, cyano, or glycosyl functional groups; or
(iii) an amino acid residue of formula (VI a) or (VI b)

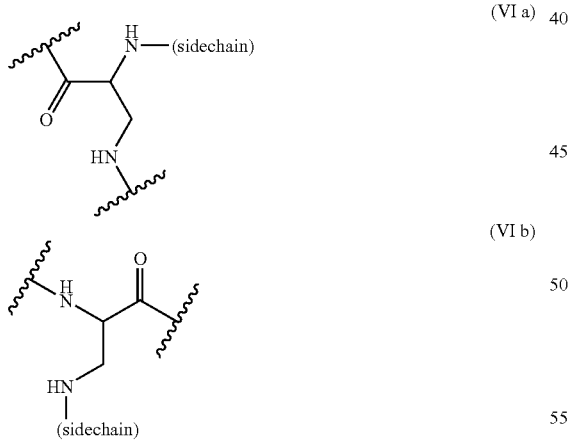

wherein
when —N$^1$—, —N$^2$— or —N$^3$— are α- or β-(homo) amino acids and when these amino acids contain a chiral carbon atom, they are optionally D- or L-; and
when —N$^1$— or —N$^2$— are α- or β-(homo) amino acids, then they are optionally in the N—C$_1$-C$_6$-alkyl form; or
—N$^1$— is a ω-amine-linked D- or L-diamino acid of the structure HOOC—CH(NH$_2$)—(CH$_2$)$_p$—NH$_2$, or
—N$^3$— is D-Dap, L-Dap, D-(β)Dap, L-(β)Dap or a ω-amine-linked amino acid of the structure HOOC —(CH$_2$)$_p$—CH(NH$_2$)CH$_2$—NH$_2$, wherein p is an integer of 1 to 10, wherein the remainder of the peptide toward the N-terminus is linked at either amine group, and wherein (β)Dap means β-diaminopropionic acid.

19. The conjugate according to claim 18, wherein
—N$^1$— is (β)Dap(COCH$_2$CH$_2$NH$_2$),
—N$^2$— is Gly;
(β)Dap(COCH$_2$CH$_2$NH$_2$) represents an amino acid residue of formula (VI a), and -(sidechain) is —COCH$_2$CH$_2$NH$_2$.

20. A compound PG comprising
(a) the peptide P
wherein the peptide P contains from 4 to 20 amino acid residues, and including a complexing amino acid sequence comprising
(i) a tridentate or tetradentate planar chelator containing a ligand backbone defined by a perimeter containing
a single sulfur donor atom,
two or three non-sulfur donor atoms, and
intervening atoms between the donor atoms; and
(ii) a stabilizing sidechain comprising a further donor atom, the further donor atom being covalently linked to the ligand backbone of the planar chelator through two or three intervening atoms, provided that
said further donor atom is neither the nitrogen nor the oxygen atom of a peptide bond, and
if said further donor atom is part of a heterocyclic ring, no more than one of the intervening atoms can be part of that ring; and
(iii) a radioactive metal complexed to the donor atoms of the planar chelator,
wherein the planar chelator comprises a single thiol amino acid or single thiol moiety containing the single sulfur donor atom of the ligand backbone, the single thiol amino acid or single thiol moiety having a structure of formula (I)

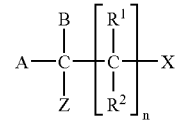

wherein
A is —CO$_2$H, —CONH$_2$, —CO$_2$-(pep), —CONH-(pep), or R$^4$;
B is —SH, —NHR$^3$, —N(R$^3$)-(pep), or R$^4$;
X is —SH, —NHR$^3$, —N(R$^3$)-(pep), or R$^4$;
Z is —H or CH$_3$;
n is 0, 1, or 2;
R$^1$, R$^2$, R$^3$, and R$^4$ are independently —H or —C$_1$-C$_6$-alkyl;
(pep) represents the remainder of the peptide P and its complexing amino acid sequence, respectively;
provided that either
(i) B is —SH; X is —NHR$^3$ or —N(R$^3$)-(pep); and n is 1 or 2; or
(ii) A is R$^4$; B is —SH; and X is —N(R$^3$)-(pep); or
(iii) A is R$^4$; B is —N(R$^3$)-(pep); and X is —SH; or
(iv) A is —CO$_2$-(pep) or —CONH-(pep); B is —SH; X is —CH$_3$; Z is —CH$_3$; and n is 0;
(b) a functional group G capable of reacting with a targeting moiety T, wherein the functional group G is carboxyl, activated carboxyl, amino, aldehyde, hydrazine, semicarbazide, thiosemicarbazide, isocyanate, isothiocyanate, imino ester, maleine imide, alkenyl, alkenylene, dienyl, dienylene, alkynyl, alkynylene, α-halocarbonyl, halosulfonyl, haloacetamide, acylamino, mixed anhydride, azide, hydroxy, carbodiimide, α,β-unsaturated carbonyl or haloacetyl, wherein halo means fluoro, chloro, bromo or iodo.

21. A conjugate PGT comprising
   (a) the peptide P
   wherein the peptide P contains from 4 to 20 amino acid residues, and including a complexing amino acid sequence comprising
   (i) a tridentate or tetradentate planar chelator containing a ligand backbone defined by a perimeter containing
      a single sulfur donor atom,
      two or three non-sulfur donor atoms, and
      intervening atoms between the donor atoms; and
   (ii) a stabilizing sidechain comprising a further donor atom, the further donor atom being covalently linked to the ligand backbone of the planar chelator through two or three intervening atoms, provided that
      said further donor atom is neither the nitrogen nor the oxygen atom of a peptide bond, and
      if said further donor atom is part of a heterocyclic ring, no more than one of the intervening atoms can be part of that ring; and
   (iii) a radioactive metal complexed to the donor atoms of the planar chelator,
      wherein the planar chelator comprises a single thiol amino acid or single thiol moiety containing the single sulfur donor atom of the ligand backbone, the single thiol amino acid or single thiol moiety having a structure of formula (I)

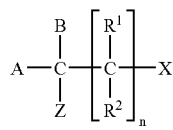

(I)

wherein
A is —CO$_2$H, —CONH$_2$, —CO$_2$-(pep), —CONH-(pep), or R$^4$;
B is —SH, —NHR$^3$, —N(R$^3$)-(pep), or R$^4$;
X is —SH, —NHR$^3$, —N(R$^3$)-(pep), or R$^4$;
Z is —H or —CH$_3$;
n is 0, 1, or 2;
R$^1$, R$^2$, R$^3$, and R$^4$ are independently —H or —C$_1$-C$_6$-alkyl;
(pep) represents the remainder of the peptide P and its complexing amino acid sequence, respectively;
provided that either
   (i) B is —SH; X is —NHR$^3$ or —N(R$^3$)-(pep); and n is 1 or 2; or
   (ii) A is R$^4$; B is —SH; and X is —N(R$^3$)-(pep); or
   (iii) A is R$^4$; B is —N(R$^3$)-(pep); and X is —SH; or
   (iv) A is —CO$_2$-(pep) or —CONH-(pep); B is —SH; X is —CH$_3$; Z is —CH$_3$; and n is 0;
(b) a functional group G which has been reacted with a targeting moiety T, wherein the functional group G before reaction with the targeting moiety T, was carboxyl, activated carboxyl, amino, aldehyde, hydrazine, semicarbazide, thiosemicarbazide, isocyanate, isothiocyanate, imino ester, maleine imide, alkenyl, alkenylene, dienyl, dienylene, alkynyl, alkynylene, α-halocarbonyl, halosulfonyl, haloacetamide, acylamino, mixed anhydride, azide, hydroxy, carbodiimide, α,β-unsaturated carbonyl or haloacetyl,
   wherein halo means fluoro, chioro, bromo or iodo, and
(c) targeting moiety T is covalently linked to functional group G.

22. The conjugate according to claim 1, wherein the targeting moiety T is a polyacetal, oligoacetal, polyester, oligoester, polyamide, oligoamide, polyolefin, oligoolefin, glycoprotein, lipoprotein, antibody, glycane, vector amine, biogene amine, pharmaceutical drug, bioactive lipid, lipoid, fatty acid ester, triglyceride, liposome, porphyrin, texaphrin, cytochrome, an inhibitor, neuramidase, prostaglandin, endotheline, alkaloid, vitamin or an analogue, hormone, anti-hormone, DNA-intercalator, nucleoside, nucleotide, lectin, peptide, antibody fragment, camelid, diabody, minibody, receptor agonist, receptor antagonist, or aptamer.

23. The conjugate according to claim 22, wherein the targeting moiety T comprises a targeting amino acid sequence and that the conjugate in total comprises at least 7, but not more than 500 amino acid residues.

24. The conjugate according to claim 23, wherein the total number of amino acid residues in the peptide P and the targeting moiety T does not exceed 100.

25. The conjugate according to claim 22, wherein the targeting moiety T comprises a targeting amino acid sequence which is a somatostatin receptor binding peptide, cyclic GPIIb/IIIa receptor binding peptide, leukocyte binding peptide, peptide derived from platelet factor 4, vasoactive intestinal peptide receptor binding peptide, neuropeptide Y receptor binding peptide, alpha-melanocyte- stimulating hormone receptor binding peptide, neurotensin receptor binding peptide, urokinase plasminogen activator receptor binding peptide, gastrin releasing peptide receptor binding peptide, α(v)β(3) receptor binding peptide, cholecystokinin receptor binding peptide, calcitonin receptor binding peptide, or chemotactic peptide.

26. A pharmaceutical composition comprising a conjugate as defined in claim 1 and a pharmaceutically acceptable carrier.

* * * * *

UNITED STATES PATENT AND TRADEMARK OFFICE
CERTIFICATE OF CORRECTION

PATENT NO. : 7,481,993 B2
APPLICATION NO. : 11/371241
DATED : January 27, 2009
INVENTOR(S) : John Cyr Page 1 of 1

It is certified that error appears in the above-identified patent and that said Letters Patent is hereby corrected as shown below:

Column 48, line 39, reads "(2-naphthyl) –$C_6H_{11}$," should read -- 2-naphthyl), –$C_6H_{11}$, --

Column 48, line 59, reads "$N^3$;" should read -- $N^3$; --

Column 51, line 21, reads "—$SR^{26}$,or" should read -- —$SR^{26}$, or --

Column 51, line 52, reads "4to6" should read -- 4 to 6 --

Column 58, line 16, reads "chioro," should read -- chloro, --

Signed and Sealed this

Eleventh Day of August, 2009

David J. Kappos
*Director of the United States Patent and Trademark Office*

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Cys Ala
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Met Cys Ala
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Orn

<400> SEQUENCE: 3
```

```
Gly Gly Xaa Cys Ala
 1               5
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Orn

<400> SEQUENCE: 4

```
Gly Xaa Gly Cys Ala
 1               5
```

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Gly Gln Cys Ala
 1               5
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly Gly Glu Cys Ala
 1               5
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-Dap

<400> SEQUENCE: 7

```
Gly Xaa Gly Cys Ala
 1               5
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Beta-Dap

```
<400> SEQUENCE: 8

Gly Xaa Met Cys Ala
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Gly Gly Gly Cys Ala
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Orn

<400> SEQUENCE: 10

Tyr Gly Gly Xaa Cys Ala
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Gly Met Gly Cys Ala
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Gly Gln Gly Cys Ala
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Gly Glu Gly Cys Ala
 1               5
```

```
<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Gly Gly His Cys Ala
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Beta-Dap

<400> SEQUENCE: 15

Tyr Gly Xaa Gly Cys Ala
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Beta-Dap(COCH2CH2NH2)

<400> SEQUENCE: 16

Tyr Gly Xaa Gly Cys Ala
 1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Tyr Ala
 1
```